(12) United States Patent
Hatton et al.

(10) Patent No.: US 9,579,674 B2
(45) Date of Patent: Feb. 28, 2017

(54) ACTUATING SYSTEM FOR A FLUENT SUBSTANCE DISPENSING SYSTEM

(71) Applicant: AptarGroup, Inc., Crystal Lake, IL (US)

(72) Inventors: Jason Hatton, Essexville, MI (US); Christophe Tondenier, Belbeuf (FR); Scott Sierens, Lake In The Hills, IL (US)

(73) Assignee: APTARGROUP, INC, Crystal Lake, IL (US)

( * ) Notice: Subject to any disclaimer, the term of this patent is extended or adjusted under 35 U.S.C. 154(b) by 81 days.

(21) Appl. No.: 14/758,037

(22) PCT Filed: Feb. 27, 2015

(86) PCT No.: PCT/US2015/018013
§ 371 (c)(1),
(2) Date: Jun. 26, 2015

(87) PCT Pub. No.: WO2016/137494
PCT Pub. Date: Sep. 1, 2016

(65) Prior Publication Data
US 2016/0368009 A1    Dec. 22, 2016

(51) Int. Cl.
*B65D 88/54*        (2006.01)
*G01F 11/00*        (2006.01)
(Continued)

(52) U.S. Cl.
CPC ....... *B05B 11/3001* (2013.01); *A45D 40/0075* (2013.01); *B05B 11/3047* (2013.01); *B05B 11/3064* (2013.01)

(58) Field of Classification Search
CPC ............. B05B 11/3001; B05B 11/3047; B05B 11/3064; B05B 11/3097; A45D 40/0075; B65D 23/06; B65D 47/40
(Continued)

(56) References Cited

U.S. PATENT DOCUMENTS

| 4,236,651 A | 12/1980 | Meyer et al. |
| 4,493,440 A * | 1/1985 | von Buelow ........ A47K 5/1204 222/109 |

(Continued)

OTHER PUBLICATIONS

International Search Report and Written Opinion for PCT Application No. PCT/US2015/018013, of which the present application is a U.S. National Phase Application.

*Primary Examiner* — Patrick M Buechner
*Assistant Examiner* — Benjamin R Shaw
(74) *Attorney, Agent, or Firm* — Wood, Phillips, Katz, Clark & Mortimer

(57) ABSTRACT

An actuating system is provided for a dispenser cartridge that can be mounted on a frame and that has a reciprocatable product-dispensing hollow stem that (A) is biased to an extended position in which the cartridge is unactuated, and (B) is moveable from the extended position to a depressed position in which the cartridge is actuated for discharging the fluent substance through the stem. The actuating system includes a plunger on the frame, and a discharge conduit located adjacent the frame to accommodate relative movement between the discharge conduit and the frame. The discharge conduit includes (A) ml inlet opening communicating with the dispenser cartridge hollow stem, (B) ml outlet opening from which the fluent substance can be dispensed, (C) a passageway between the inlet opening and outlet opening, and (D) an intermediate opening that is in communication with the passageway between the inlet opening and the outlet opening.

13 Claims, 16 Drawing Sheets

(51) Int. Cl.
*B05B 11/00* (2006.01)
*A45D 40/00* (2006.01)

(58) Field of Classification Search
USPC .................. 222/380, 108, 321.2, 321.3, 252,
265,222/275, 276, 280, 255, 207, 209,
212, 213, 214
See application file for complete search history.

(56) References Cited

U.S. PATENT DOCUMENTS

| | | | | |
|---|---|---|---|---|
| 4,515,294 A * | 5/1985 | Udall | .................... | A47K 5/1209 |
| | | | | 222/105 |
| 4,570,829 A * | 2/1986 | Allen | ..................... | B65D 35/40 |
| | | | | 222/181.2 |
| 4,776,495 A * | 10/1988 | Vignot | ................. | A47K 5/1209 |
| | | | | 222/206 |
| 8,708,200 B2 * | 4/2014 | Nilsson | ................ | A47K 5/1209 |
| | | | | 222/207 |
| 8,757,454 B2 * | 6/2014 | Dong | ................. | B05B 11/3097 |
| | | | | 222/321.3 |
| 2003/0042272 A1 | 3/2003 | Rousselet et al. | | |
| 2007/0272710 A1 * | 11/2007 | Bui | ...................... | B01L 3/0265 |
| | | | | 222/207 |
| 2009/0184134 A1 * | 7/2009 | Ciavarella | ................ | A47K 5/14 |
| | | | | 222/135 |
| 2015/0090737 A1 * | 4/2015 | Ciavarella | ............ | A47K 5/1211 |
| | | | | 222/190 |

* cited by examiner

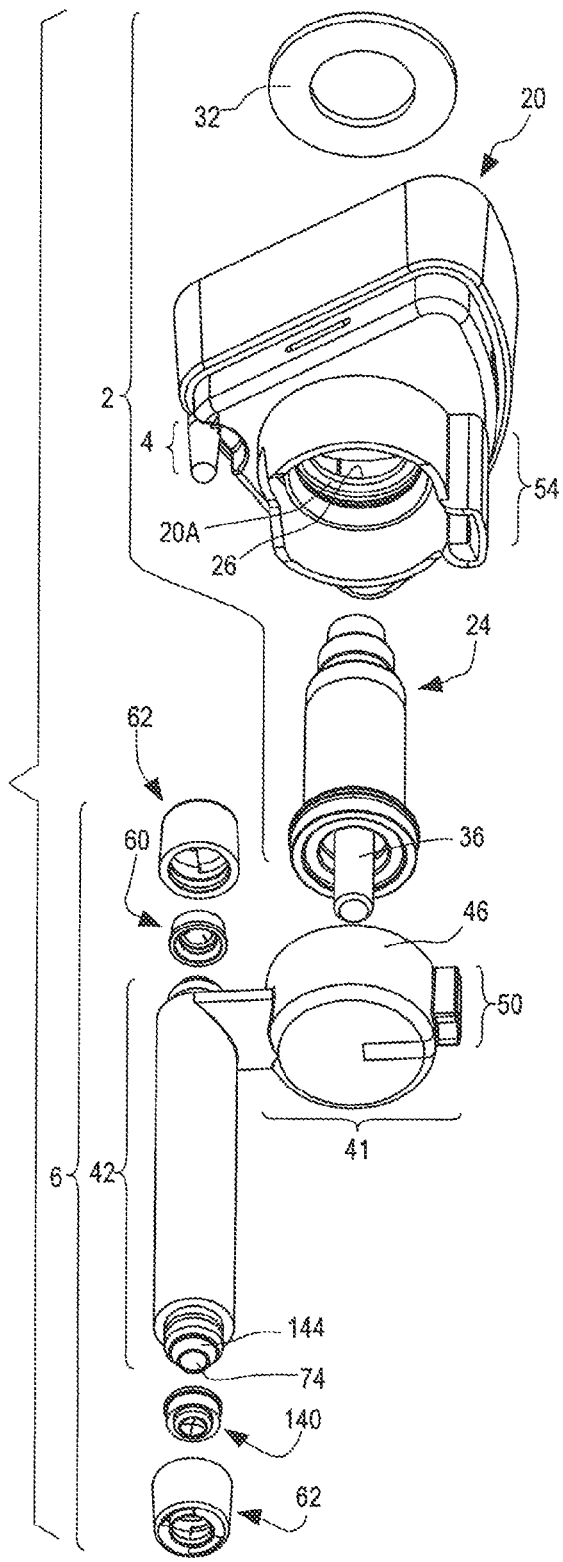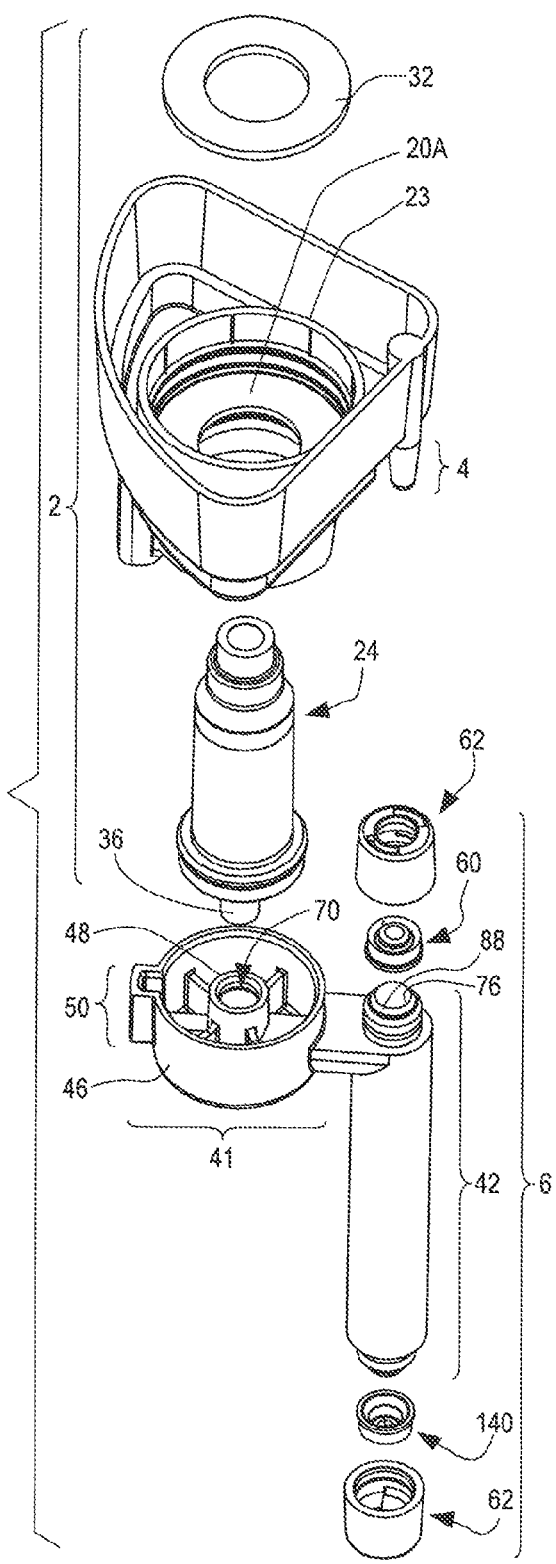

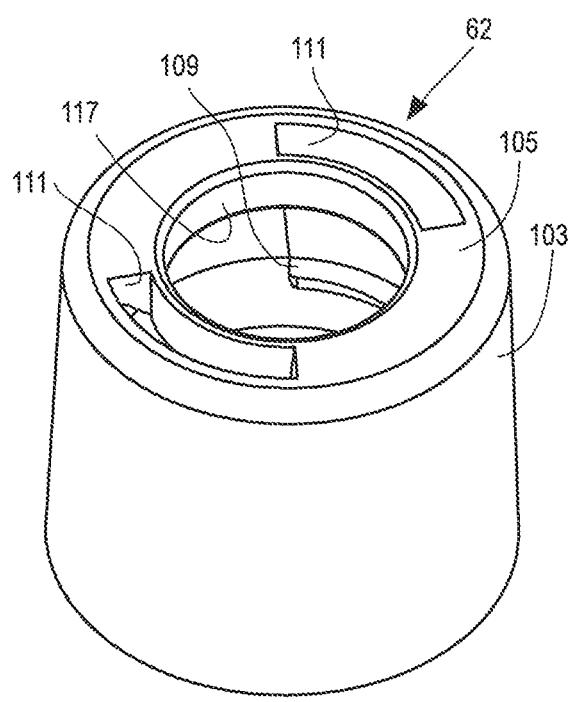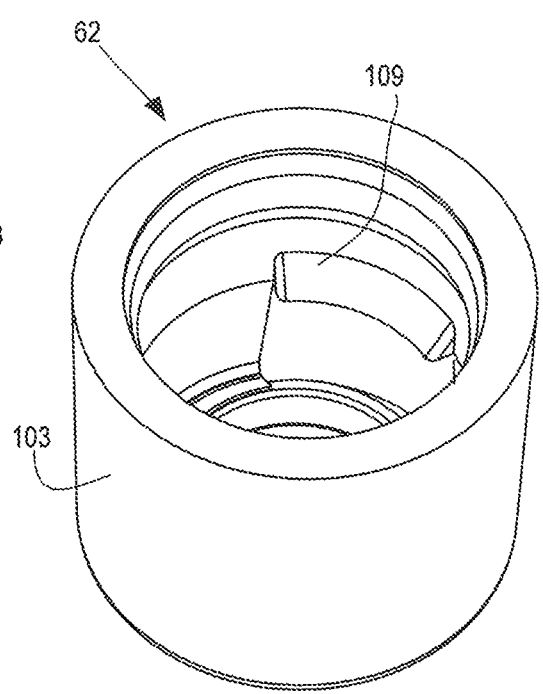

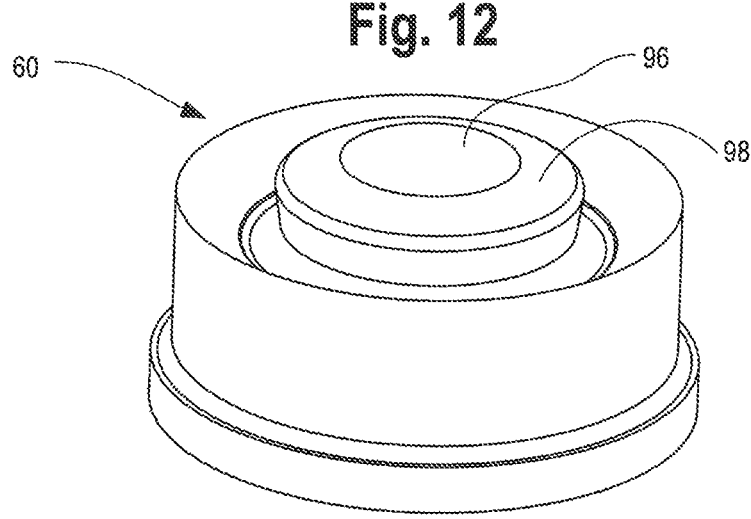
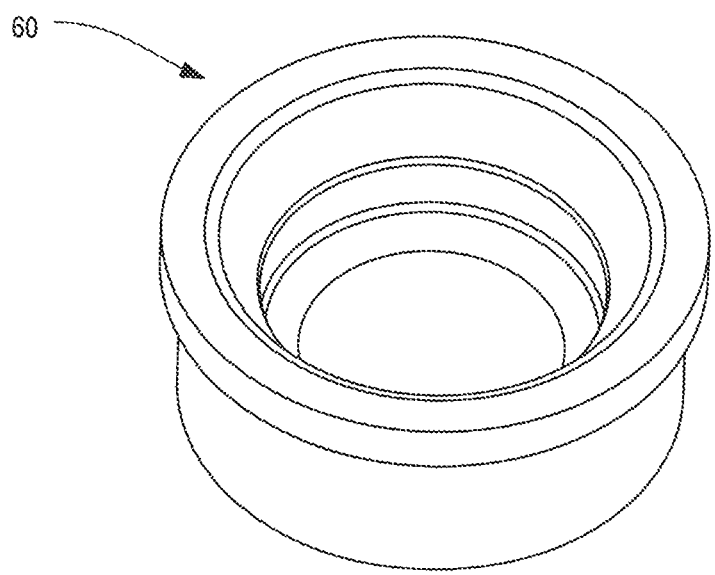

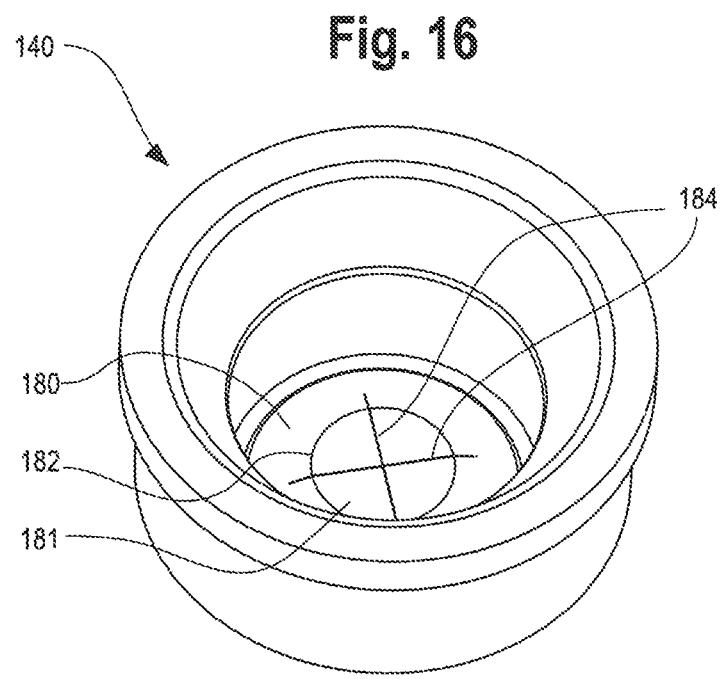
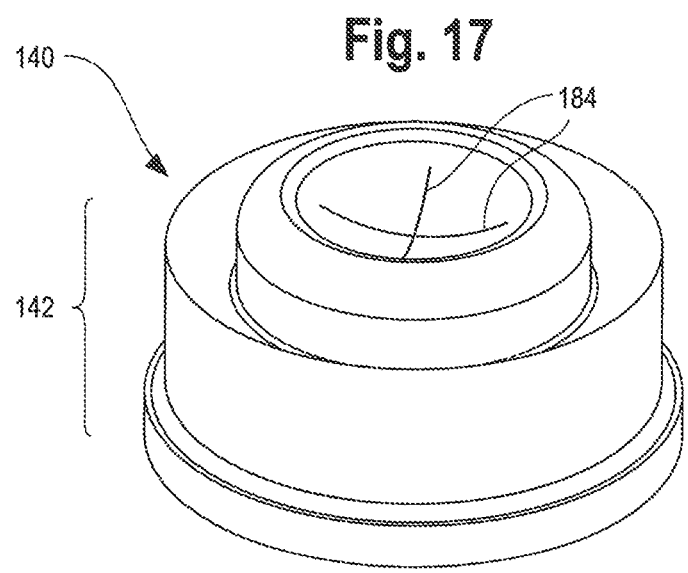

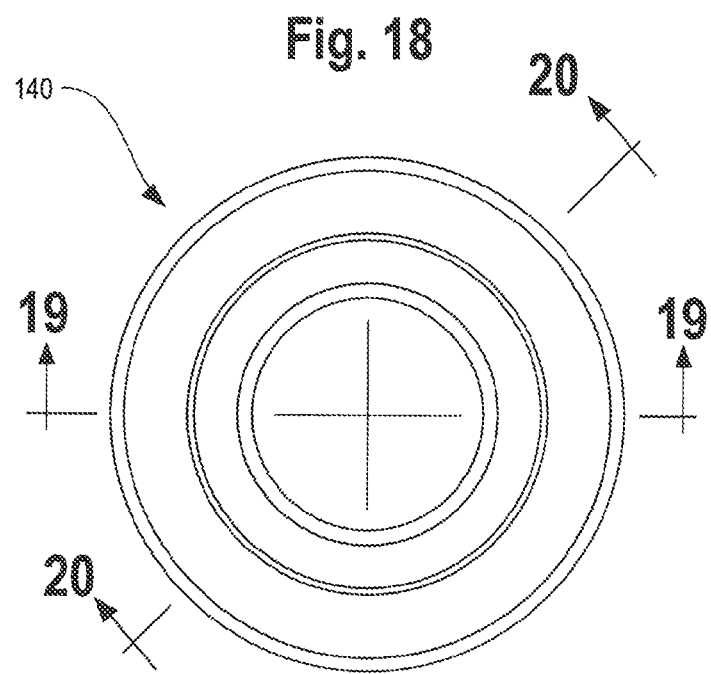
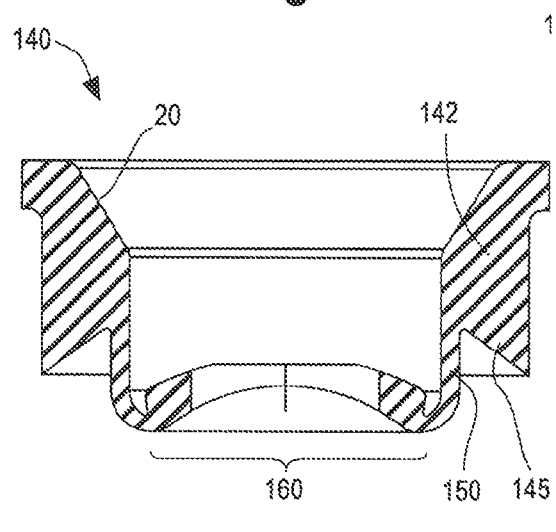
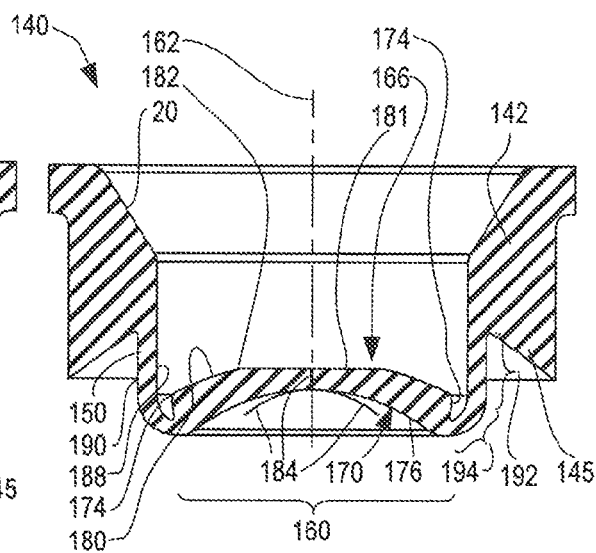

ACTUATING SYSTEM FOR A FLUENT SUBSTANCE DISPENSING SYSTEM

CROSS-REFERENCE TO RELATED APPLICATION(S)

Not Applicable.

STATEMENT REGARDING FEDERALLY SPONSORED RESEARCH OR DEVELOPMENT

Not applicable.

REFERENCE TO A MICROFICHE APPENDIX

Not applicable.

TECHNICAL FIELD

This invention relates to an actuating system for a fluent substance dispensing system.

BACKGROUND OF THE INVENTION AND TECHNICAL PROBLEMS POSED BY THE PRIOR ART

In some situations, it may be desirable to dispense a substance in a convenient manner from a supply of the substance to a receiver or target region. For example, it may be desirable to dispense a human body skin care moisturizing lotion or cream from a container through a discharge spout or conduit to a person's hand or other body part. Examples of finger-actuated pumps for dispensing lotions, creams, etc. from a small container onto a person's hand are disclosed in the U.S. Pat. No. 4,991,746, No. 6,332,561, and No. 6,364,181.

The inventors of the present invention have observed that after a quantity of a lotion or similar substance has been dispensed from some types of dispensers, a residual drop or residue of the substance sometimes remains hanging like a "tail" from the end of the discharge spout or conduit. Such a residual, hanging tail of the substance might be more likely to occur and/or be more pronounced in a dispenser wherein the substance is relatively viscous and/or wherein a portion of the spout or discharge conduit is vertically oriented at the discharge opening. The inventors of the present invention have discovered that, at least in some applications, the existence of a hanging tail of the substance may be aesthetically undesirable and/or may even result in an unwanted deposit of the substance if the tail later drops or falls away.

The inventors of the present invention have determined that for at least some applications using some types of dispensers to dispense some types of fluent substances, it may be desirable to provide an actuating system that can eliminate, or at least reduce or substantially minimize, the formation of a residual tail of the substance hanging from the discharge opening of the discharge conduit.

The inventors of the present invention have further determined that it would be beneficial to provide an improved actuating system for a dispensing system containing a substance (i.e., product) that can be readily applied to a target region. Such an actuating system could be advantageously employed in a variety of applications, including, but not limited to, applications for dispensing consumer products, for example, cosmetic products.

The inventors of the present invention have also discovered that it would be desirable to provide, at least for one or more types of products (i.e., substances), an improved actuating system that can be configured with the dispensing system so as to permit the systems to have one or more of the following attributes or features:

A. a design that prevents, or at least reduces, the ingress of dirt or other contaminants from the exterior environment, and B. a design that prevents, or at least reduces, leakage of the product and reduces or minimizes messiness.

The inventors of the present invention have also discovered that it would be desirable to provide, at least for one or more types of products (i.e., substances), an improved actuating system that can be configured with the dispensing system so as to have one or more of the following advantages:

A. ease of manufacture and/or assembly, and

B. low cost manufacture and/or assembly.

BRIEF SUMMARY OF THE INVENTION

The inventors of the present invention have discovered how to provide an improved actuating system which can be used with a fluent substance dispensing system, and which can eliminate, or at least minimize or reduce, the formation of a residual tail of the substance hanging from the discharge opening of a discharge conduit.

The actuating system is adapted for use with a fluent substance dispensing system wherein the dispensing system includes (A) a frame, and (B) a dispenser cartridge that (1) can be mounted on the frame in communication with a fluent substance; and (2) has a reciprocatable, product-dispensing hollow stem that is (i) biased to an extended position in which the cartridge is unactuated, and (ii) movable from the extended position to a depressed position in which the cartridge is actuated for discharging the fluent substance through the stem.

The actuating system comprises (A) a plunger on the frame; and (B) an actuator. The actuator includes a discharge conduit that is located adjacent the frame to accommodate relative movement between the discharge conduit and the frame toward and away from each other. The discharge conduit defines: (1) an inlet opening that can be located in fluid communication with the cartridge hollow stem for receiving a fluent substance discharged from the cartridge hollow stem when the cartridge is actuated; (2) an outlet opening from which a fluent substance can be discharged; (3) a passageway between the inlet opening and the outlet opening; and (4) an intermediate opening that (i) is in communication with the passageway between the inlet opening and the outlet opening, and (ii) can receive the plunger.

The actuator of the actuating system further includes a distendable, resilient membrane that (1) is located across the intermediate opening; (2) is distended by the plunger during relative movement between the frame and the discharge conduit toward each other to depress the cartridge hollow stem for discharging the fluent substance from the cartridge into the discharge conduit passageway; and (3) is less distended by the plunger during relative movement between the frame and the discharge conduit away from each other permitting the cartridge hollow stem to be biased toward the extended position in which the cartridge is unactuated and whereby ambient atmospheric pressure can force at least some of the fluent substance inwardly from the discharge conduit outlet as the volume in the passageway increases owing to the decreased distention of the membrane.

Numerous other advantages and features of the present invention will become readily apparent from the following detailed description of the invention, from the claims, and from the accompanying drawings.

BRIEF DESCRIPTION OF THE DRAWINGS

In the accompanying drawings forming part of the specification, in which like numerals are employed to designate like parts throughout the same.

FIG. 3 is an exploded, perspective view of the components shown in FIG. 2 as viewed from beneath the components;

FIG. 4 is an exploded, perspective view of the components shown in FIG. 2; but in FIG. 4 the components are viewed from above;

FIG. 7 is a top, perspective view of the retainer for the membrane;

FIG. 8 is a bottom, perspective view of the retainer shown in FIG. 7;

FIG. 12 is a top, perspective view of the membrane;

FIG. 13 is a bottom, perspective view of the membrane;

FIG. 16 is a top, perspective view looking into the inside of the valve;

FIG. 17 is a bottom, perspective view of the valve shown in FIG. 16;

FIG. 18 is a top, plan view of the valve shown in FIGS. 16 and 17;

FIG. 19 is a cross-sectional view taken generally along the plane 19-19 in FIG. 18;

FIG. 20 is a cross-sectional view taken generally along the plane 20-20 in FIG. 18;

DESCRIPTION OF THE PREFERRED EMBODIMENTS

While the actuating system of this invention is susceptible of embodiment in many different forms, this specification and the accompanying drawings disclose only some specific forms as examples of the invention. The invention is not intended to be limited to the embodiments so described, however.

For ease of description, the actuating system of this invention is described in a generally vertical orientation in cooperation with a fluent substance dispensing system. It will be understood, however, that this invention may be manufactured, stored, transported, used, and sold in orientations other than those shown.

The actuating system of this invention is suitable for use with a variety of conventional or special fluent substance dispensing systems having various designs, the details of which, although not illustrated or described, would be apparent to those having skill in the art and an understanding of such systems.

Figures illustrating the components of this actuating system invention in cooperation with a dispensing system show some conventional mechanical elements that are known and that will be recognized by one skilled in the art. The detailed descriptions of such elements are not necessary to an understanding of the invention, and accordingly, are herein presented only to the degree necessary to facilitate an understanding of the novel features of the present invention.

Figure 1:
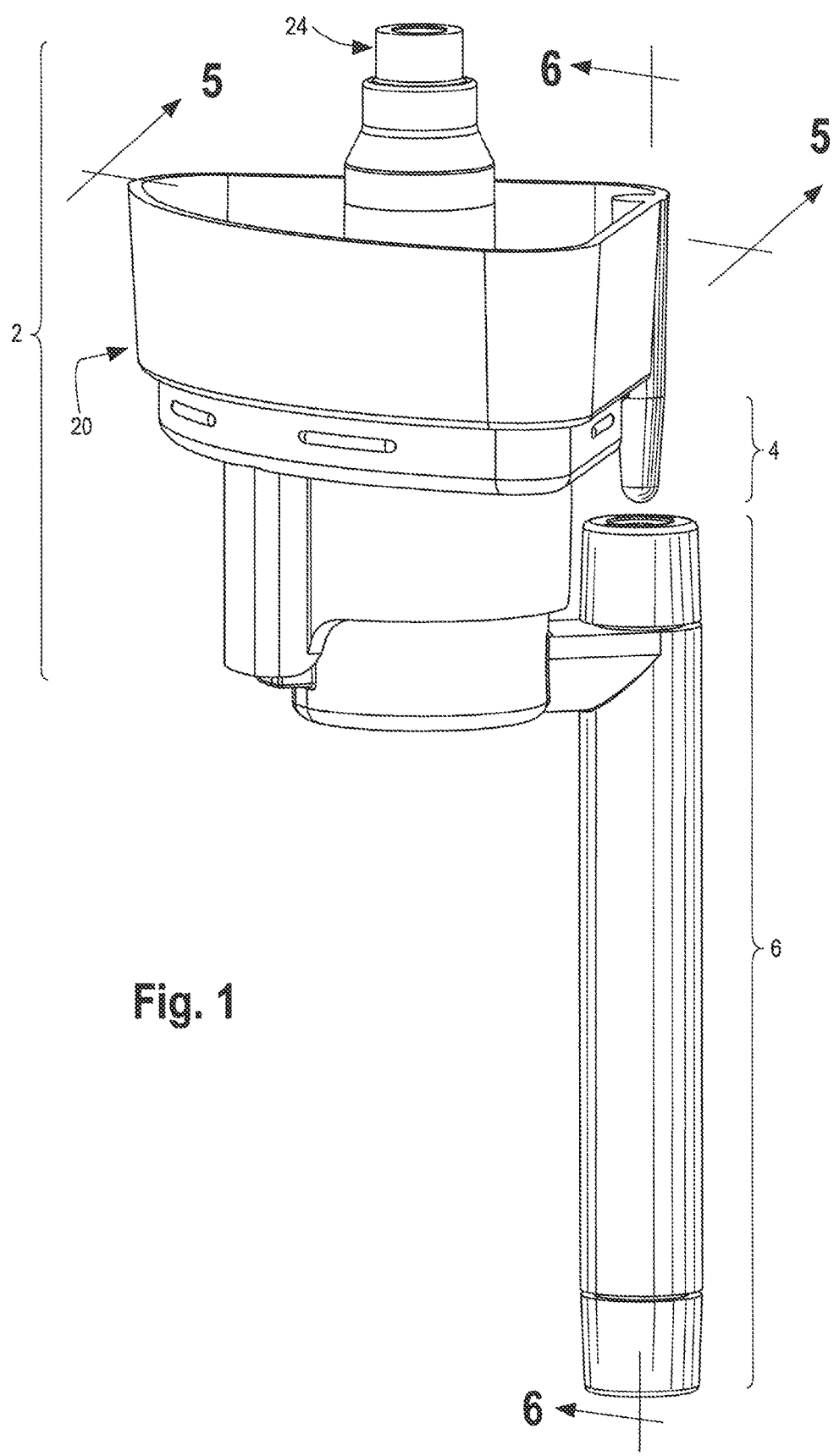
FIG. 1 is a perspective view of a fluent substance dispensing system in a cooperative arrangement with the actuating system of the present invention shown with the fluent substance dispensing system in an unactuated condition prior to installation of a fluent substance container (not shown) in the dispensing system.
Figure 2:
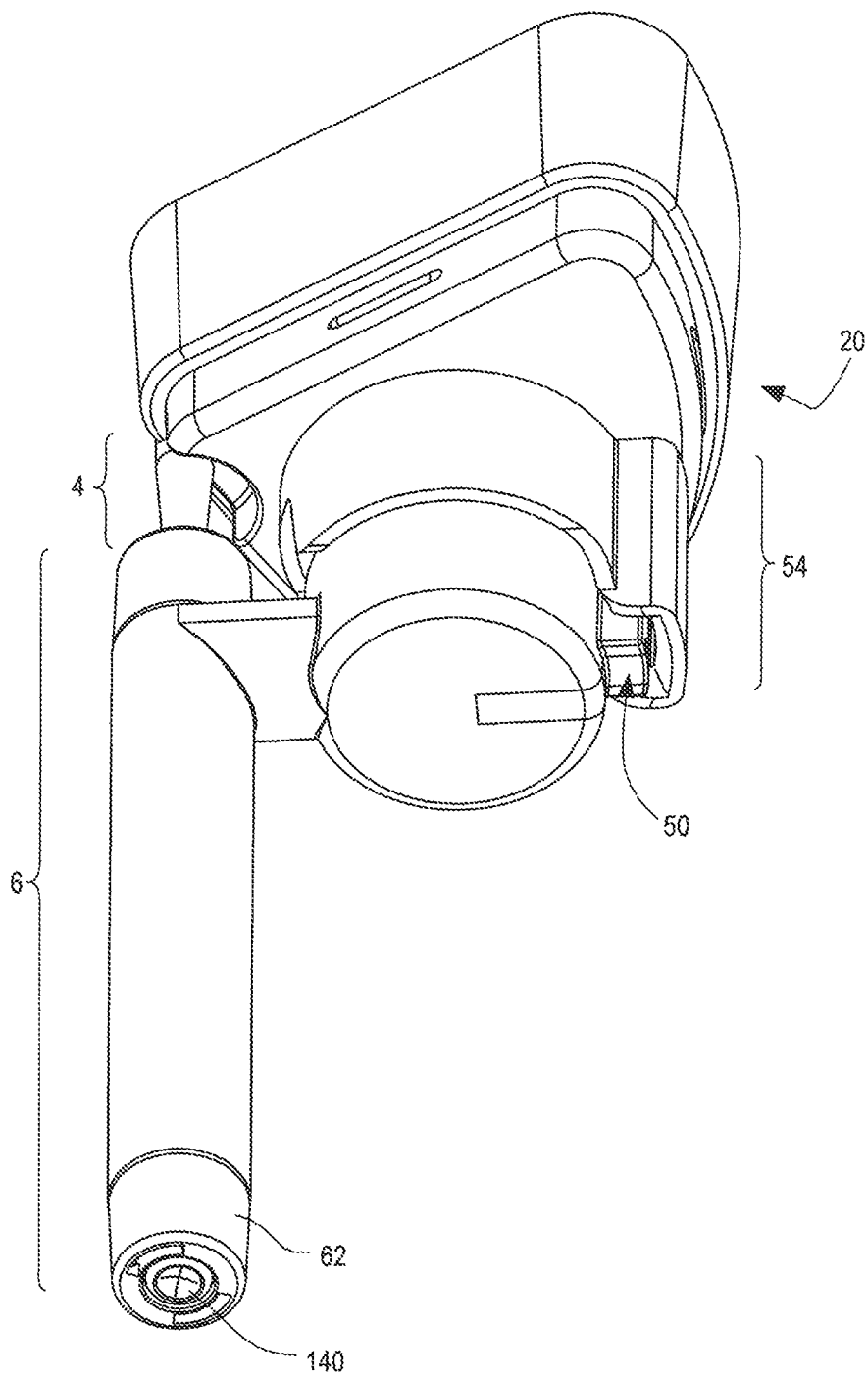
FIG. 2 is a perspective view of the components of FIG. 1, but the FIG. 2 perspective view is taken from below the components.
Figure 5:
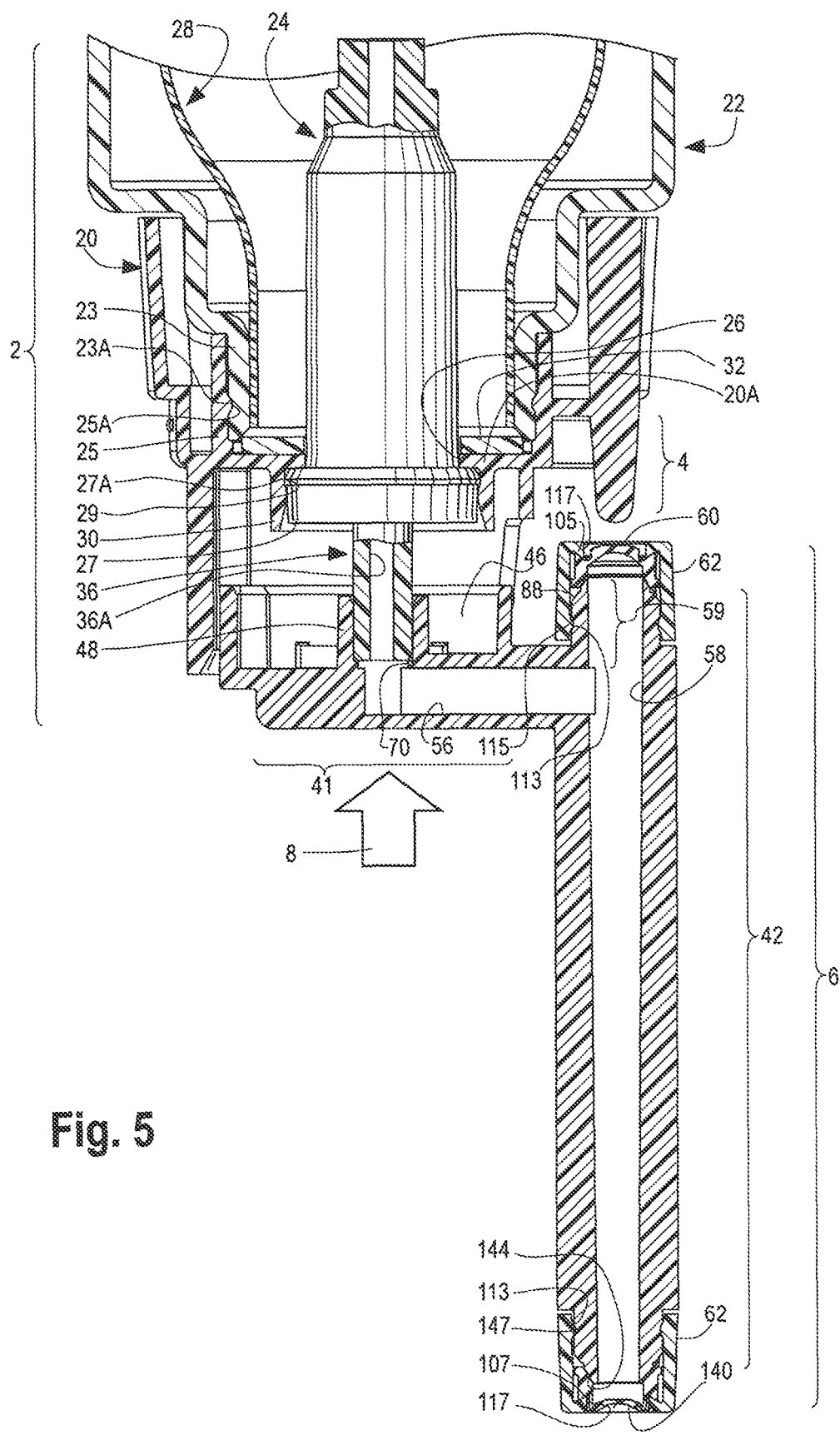
FIG. 5 is a fragmentary, cross-sectional view taken generally the plane 5-5 in FIG. 1, and in FIG. 5 a portion of the installed fluent substance container is shown.

With reference to FIGS. 1-5, a fluent substance dispensing system 2 is shown in operative association with the actuating system of the present invention which comprises an actuator 6 and a cooperating plunger 4 that extends from the framework of the dispensing system 2. With reference to FIG. 5, the fluent dispensing system 2 includes a container 22 which contains a supply of a fluent substance, but the container 22 has been omitted from FIGS. 1, 2, 3, and 4 for purposes of showing interior details of the other dispensing system components and for ease of illustration. The container 22 is described in more detail hereinafter.

In the embodiment illustrated, the actuator 6 is adapted to be moved by suitable means toward a portion of the fluent substance dispensing system 2 to which the plunger 4 is attached (compare FIG. 5 with FIG. 21), and this movement may be effected by pushing the actuator 6 with a person's finger or by pushing the actuator 6 with a suitable device (e.g., an electromechanical operator such as a gear motor assembly with cam driver pusher plates (not illustrated)). In FIG. 5, such a manual or mechanical means for pushing on the actuator 6 to move it toward a portion of the dispensing system 2 is schematically or diagrammatically represented by a large arrow 8. According to the broad principles of the present invention, in an alternate method of operation, the actuator 6 could instead remain stationary while a portion of the dispensing system 2 is moved toward the actuator 6. In yet another form of the operation, movement of both a portion of the dispensing system 2 and the actuator 6 toward each other could be effected. The positions of the actuator 6 and dispensing system 2 closer to each other defines an actuating, or actuated, condition for dispensing a product as explained in detail hereinafter.

Figure 21:
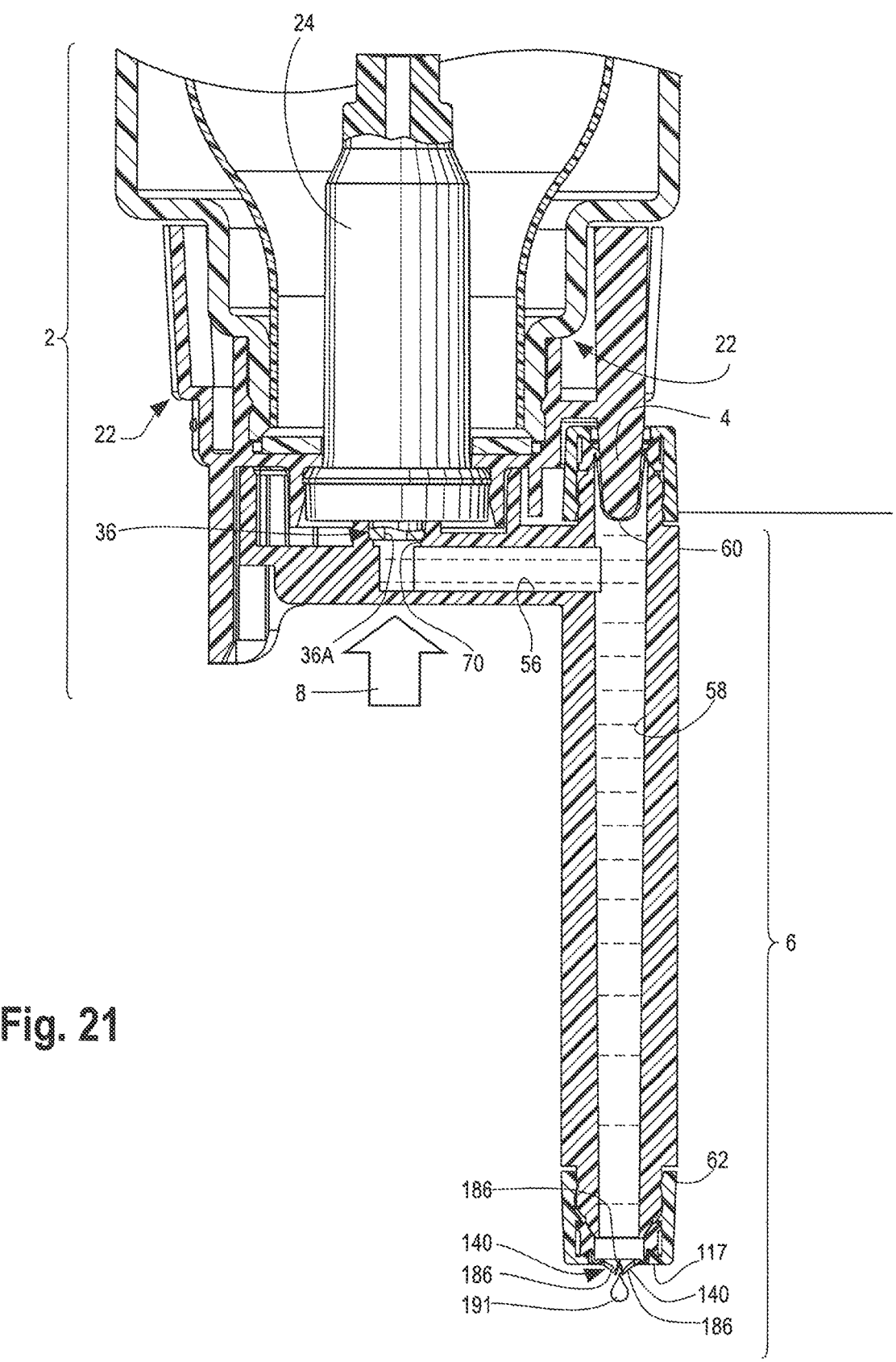
FIG. 21 is a cross-sectional view similar to FIG. 5, but in FIG. 21, the actuator portion of the actuating system is shown in an upwardly moved position actuating the fluent substance dispensing system to dispense a drop of a fluent substance through the open valve at the bottom end of the actuator discharge conduit.

According to the present invention, after the actuation force is terminated and no longer acting on the actuator 6, the actuator 6 accommodates relative movement between the actuator 6 and at least a portion of the dispensing system 2 (from which the actuating system plunger 4 extends) away from each other back to the unactuated, rest condition (compare FIGS. 21 and 5)—in this illustrated embodiment the actuator 6, per se, moving away from the entire dispensing system 2 which is stationary as can be seen by comparing the elevated position of the actuator 6 in FIG. 21 with the lowered position of the actuator 6 in FIG. 5. Such a downward movement may be effected by, for example, (1) gravity, and/or (2) a spring force exerted by the dispensing system 2 on the actuator 6 (as explained in detail hereinafter), and/or (3) a force exerted by another device (e.g., an electromechanical operator (not shown)) acting on the actuator 6. According to a broad aspect of the present invention, in an alternate embodiment (not illustrated), the actuator 6 may instead remain stationary, while at least a portion of the dispensing system 2 (carrying the actuating system plunger 4) is moved away from the actuator 6, or alternatively, both the actuator 6 and at least a portion of the dispensing system 2 can be simultaneously moved away from each other.

In the illustrated embodiments of the present invention, the actuator 6 of the present invention actuating system cooperates to engage an outwardly biased discharge tube or stem of the dispensing system 2 as described in detail hereinafter, but the inventive actuating system components (i.e., the plunger 4 and actuator 6) do not include the operative components of the dispensing system 2, per se.

The Dispensing System

The actuating system of the present invention is adapted to be used with a fluent substance dispensing system 2 that includes an outwardly biased, reciprocatable, dispensing member (such as a dispenser cartridge hollow stem 36 shown in FIG. 5 and described in detail hereinafter). Such a dispensing member or stem 36 is outwardly biased to an extended position at which the dispensing system 2 is not actuated, but the fluent substance can be discharged through the stem 36 when the stem 36 is depressed as explained in detail hereinafter.

The illustrated form of the dispensing system 2 holds a supply of the fluent substance in the container 22 (FIG. 5) that has a mouth or opening which provides access to the container interior where the fluent substance contents may be contained. The fluent substance is a substance that can flow, at least when subjected to a pressure differential. Such a substance may be, for example, a cosmetic lotion or cream, or other personal care product, industrial or household product, or other substance.

The illustrated form of the dispensing system 2 includes a frame 20 (FIG. 1) for holding the container 22 (FIG. 5) and a dispenser cartridge 24 (FIG. 5). The particular form of the illustrated frame 20 may also be characterized as a "snapping ring" or "snap ring" because it serves to hold the container 22 and dispenser cartridge 24 each in a snap-fit engagement as explained in detail hereinafter.

One end of the container 22 has a neck 23 (FIG. 5) that receives an inlet end of the dispenser cartridge 24 and that has an exterior cross-sectional configuration with which the frame 20 is adapted to engage. The container neck 23 has an annular groove 23A (FIG. 5), and the frame 20 has a collar 25 (FIG. 5) defining an interior annular bead 25A for snap-fit engagement with the annular groove 23A on the container neck 23. The frame 20 and container 22 may employ other mating, or cooperating, attachment features, such as a thread arrangement, for example. Also, the frame 20 and container 22 could be permanently connected, as with adhesive, etc.

The main body of the container 22 may have a cross-sectional configuration that differs from the cross-sectional configuration of the container neck 23. In a variation (not illustrated), the container 22 may have a substantially uniform shape along substantially all of its length or height without a neck portion of any significantly reduced size or significantly different cross-section.

As seen in FIG. 5, the dispenser cartridge 24 may be a "pump" dispenser cartridge 24 that is part of the dispensing system 2 and that is adapted to be mounted in the frame 20 so that a part of the pump dispenser cartridge 24 extends into the mouth of the container 22. The inner end of the pump dispenser cartridge 24 communicates with the fluent substance in the container 22, and the outer end of the pump dispenser cartridge 24 projects outwardly from the container neck 23 through an opening 26 (FIGS. 4 and 5) in a deck 20A of the frame 20.

The outer end of the pump dispenser cartridge 24 includes a radially outwardly projecting flange 27 (FIG. 5) defining an annular peripheral bead 27A to establish a snap-fit engagement with an annular groove 29 of a collar 30 that projects downwardly from the frame 20 around the opening 26 in the support frame deck 20A. A conventional sealing gasket 32 (FIG. 5) is employed between the rim of the container neck 23 and the frame deck 20A around the pump dispenser cartridge 24. Other mating or cooperating connection features on the frame 20 and dispenser cartridge 24 may be employed, and such other connection features could be a thread arrangement or other conventional or special connection features, including non-releasable connection features such as adhesive, thermal bonding, staking, etc.

The container 22 may be made from any suitable material, such as metal, glass, or plastic, and the container 22 is adapted to hold a product (e.g., a liquid (e.g., a lotion or cream, not shown)) in communication with the pump dispenser cartridge 24. In the illustrated dispensing system 2, the dispenser cartridge 24 may be an "air less" type of pump dispenser cartridge 24 (such as the type disclosed in U.S. Pat. No. 6,332,561), and the container 22 can include an internal, flexible, collapsible bag or pouch 28 (FIG. 5) which contains the product for being dispensed by the airless pump dispenser cartridge 24.

As can be seen in FIG. 5, the container bag or pouch 28 has an open end sealingly secured to the container 22 around the inside of the container neck 23 to isolate the product from the atmosphere that surrounds the pouch 28 in the container 22. During the dispensing of the product through the pump dispenser cartridge 24, the pouch 28 collapses as the product is removed from the pouch 28 by actuation of the pump dispenser cartridge 24 as explained in detail hereinafter.

When an "airless" pump dispenser cartridge 24 is employed, any suitable conventional or special design may be employed. For example, see U.S. Pat. No. 6,332,561 which discloses an airless pump that can be employed as the pump dispenser cartridge 24 with the container 22 in the dispensing system 2. The body of the airless pump dispenser cartridge 24 defines an interior chamber (not visible in the Figures of the instant patent application). The pump interior chamber contains, inter alia, (1) an inwardly extending portion of the stem 36 (FIG. 5) which is a hollow discharge tube that extends slidably through the outer end of the body of the pump cartridge 24, (2) an annular, pressurizing piston (not visible) slidably mounted on the stem, (3) a helical pre-compression sprint (not visible) acting between the piston and a flange of the stem, (4) a helical return spring (not visible) acting between the inlet end of the cartridge interior chamber and the piston so as to bias the piston against the pre-compression spring to force the piston, pre-compression spring, and stem outwardly to an unactuated, rest position when there is no opposed actuating force depressing the stem further into the cartridge 24, and (5) a non-return check valve (not visible). The check valve is disposed inside the inlet end of the interior chamber to prevent back flow when the interior chamber is pressurized by the piston during actuation of the pump.

Actuation occurs when the stem 36 is depressed (i.e., forced inwardly further in the body of the pump dispenser cartridge 24) as explained in detail hereinafter. During a dispensing actuation of the pump dispenser cartridge 24 when the stem 36 is pushed inwardly further into the body of the pump dispenser cartridge 24, the springs permit the pushing force to be transmitted by the stem 36 to the piston until a predetermined pressure is created in the pump dispenser cartridge 24, and then the increasing pressure causes compression of the pre-compression spring as the stem 36 continues moving further into the body of the cartridge 24 relative to the piston.

The hollow stem 36 defines a discharge passage 36A (FIG. 5) which, at the inner end of the hollow stem 36 in the interior chamber of the cartridge 24, is initially closed by the annular pressurizing piston, but which is opened (to dispense the product) by the relative axial movement occurring between the stem 36 and the piston during actuation of the pump dispenser cartridge 24 when the pressure becomes great enough to effect the above-discussed relative axial movement between the stem 36 and the piston.

After the pump dispenser cartridge 24 is actuated to dispense a fluent product, the user terminates the actuation operation so that the pump components are returned by the pump dispenser cartridge internal springs to the unactuated, rest condition in which the stem 36 is in the extended position (FIG. 5). As the springs move the pump piston and stem outwardly in the pump cartridge 24, the internal check valve opens, and the fluid in the container 22 is drawn into the pump dispenser cartridge 24 to refill the pump dispenser cartridge 24.

It will be appreciated that the particular design of the pump dispenser cartridge 24 may be of any suitable design for pumping a product from the container 22 and out through the stem 36. The detailed design and construction of the pump dispenser cartridge 24 (or of other types of a dispenser cartridge), per se, form no part of the present invention—it being understood that the actuating system of the invention is provided to cooperate with a pump dispenser cartridge 24 (or other type of dispensing cartridge) that is part of a fluent substance dispensing system 2 containing a supply of the fluent substance, and it being understood that the pump dispenser cartridge 24 (or other type of dispenser cartridge) includes an outwardly biased, projecting, hollow stem 36 which can be depressed for discharging the fluent substance through the stem 36 into the actuating system as explained hereinafter.

Alternate Aerosol Dispenser Cartridge

The actuating system of the present invention may be adapted for use with a dispensing system 2 that does not employ a pump dispenser cartridge, per se, but instead employs another type of dispenser cartridge 24, such as an aerosol dispenser cartridge (i.e., an aerosol dispensing valve that can dispense a pressurized fluid (e.g., a foaming lotion)). Such an aerosol dispensing valve or cartridge can be adapted to be mounted at the mouth of a container that holds a product (e.g., a fluid product). Such an aerosol dispensing valve or cartridge may be characterized as an aerosol dispenser cartridge that extends into the opening of the container. The container would typically be a metal can (not illustrated) that contains a pressurized fluid product and that is sealed to the aerosol dispenser cartridge. The aerosol dispenser cartridge may be of any suitable conventional or special type. With a typical conventional aerosol dispenser cartridge, the inner end communicates with a pressurized fluid product in the container, and the outer end projects or extends beyond the container.

Projecting from the outer end of the aerosol dispenser cartridge is a stem analogous to the previously described pump dispensing cartridge stem 36. A compression spring inside the aerosol dispenser cartridge biases the stem outwardly to an extended position projecting out of an outer end of the aerosol dispenser cartridge. Inside the cartridge there is an annular gasket through which the stem extends. The stem has an internal, longitudinally extending, central discharge passage that is open at the outer end of the stem (analogous to the passage 36A in the previously described pump dispenser cartridge stem 36 illustrated in FIG. 5). Inside the aerosol dispenser cartridge, at a location inwardly of the outer end of the stem, the stem has at least one lateral orifice which extends through the annular wall of the stem and communicates with the central discharge passage in the stem. Until the stem is depressed (by an actuating system), the lateral orifice in the stem is located adjacent, and is occluded by, the annular gasket in the aerosol dispenser cartridge. When the stem is depressed (by an actuating system), the stem is forced inwardly—compressing the spring and re-positioning the stem lateral orifice further into the dispenser cartridge body and away from the gasket so the stem lateral orifice is no longer blocked by the annular gasket, and this permits the pressurized fluid in the container and aerosol dispenser cartridge to flow through the lateral orifice into the stem central discharge passage and out of the discharge end of the stem.

After the aerosol dispenser cartridge is actuated to dispense product, and after the actuation operation is terminated, the aerosol dispenser cartridge components are returned by the internal spring to the rest condition wherein the stem is in the extended position so that the aerosol dispenser cartridge is back in the non-actuating condition.

It will be appreciated that the particular design of the aerosol dispenser cartridge (i.e., aerosol dispensing valve) may be of any suitable design for dispensing a product from a container and out through the stem. The detailed design and construction of an aerosol dispenser cartridge (or other type of dispenser cartridge), per se, form no part of the present invention—it being understood that the actuating system of the invention is provided to cooperate with an aerosol dispenser cartridge (or other type of dispenser cartridge) that is part of a fluent substance dispensing system 2 containing a supply of the fluent substance, and it being understood that the aerosol dispenser cartridge (or other type of dispenser cartridge) includes an outwardly biased, projecting, hollow stem which can be depressed for discharging the fluent substance through the stem into the actuating system as will be explained in detail hereinafter with reference to the stem 36 of the previously described pump dispenser cartridge 24.

The Actuating System

The actuating system includes the plunger 4 and the actuator 6. As seen in FIGS. 1, 3, 4, 5, and 6, the plunger 4 includes an elongate frustoconical portion extending down from the frame 20. The bottom end of the plunger 4 is defined by a generally smooth, arcuate surface which, in the illustrated preferred embodiment, is a partially hemispherical surface that faces downwardly toward the actuator 6.

The actuator 6 of the actuating system is attached to the stem 36 of the dispenser cartridge as shown in FIG. 5. The actuator 6 includes a discharge conduit, which in the embodiment illustrated in the figures, has a generally horizontal, first portion 41 and a generally vertical, second portion 42 (FIGS. 4 and 5). As can be seen in FIGS. 4 and 5, the first portion 41 of the actuator discharge conduit includes an outer housing 46 and an inner collar 48. The inner collar 48 is adapted to receive the dispenser cartridge stem 36.

In a preferred arrangement, the actuator 6 is supported at the initial, rest position shown in FIG. 5 by a suitable operator, such as an electromechanical operator (not shown), engaging the underside of the actuator discharge conduit first portion 41 as schematically represented in FIG. 5 by the large arrow 8. The detailed design and operation of an operator, or the use of a particular operator, per se, forms no part of the broad aspects of the present invention.

Such an operator can be operated to push the actuator 6 further upwardly (in the direction of the large arrow 8 in FIG. 5) to depress the dispenser cartridge stem 36 further into the dispenser cartridge 24 to actuate the dispenser cartridge 24 as previously described. Such an operator can be controlled to subsequently permit the actuator 6 to move downwardly to the initial rest position illustrated in FIG. 5, and such downward movement can occur under the influence of the internal biasing action of the dispenser cartridge spring system (not visible in the Figures) which, as previously described, acts to bias the stem 36 outwardly (downwardly as viewed in FIG. 5) to the rest elevation of the actuator 6 as illustrated in FIG. 5. Such further downward movement of the stem 36 is terminated by the engagement of an interior portion of the dispenser cartridge body with a flange on the stem 36 inside the body of the dispenser cartridge body 24. If the stem 36 is only slidably received in the actuator inner collar 48 (i.e., not fixedly connected to the actuator 6), any downward movement of the actuator 6 away from the stem 36 would be prevented by the engagement of the actuator 6 with the underlying electromechanical operator (not illustrated) or other operator at the rest position of the operator, or by a suitable travel stop (not shown) extending downwardly from the dispensing system frame 20 to engage the underside of the actuator 6 at the lowered, rest position. Thus, the dispenser cartridge stem 36 need not be fixedly attached to the actuator 6, and the bottom end of the dispenser cartridge stem 36 (i.e., the outwardly (downwardly) projecting end of the stem 36) may be merely slidably disposed within the receiving collar 48 of the first portion 41 of the actuator 6. On the other hand, if desired, the bottom end of the stem 36 could be releasably or non releasably connected to the collar 48 of the actuator 6 (e.g., by snap fit engagement means, adhesive, etc. (not illustrated)).

The vertical movement of the actuator 6 relative to the dispenser cartridge 24 and to the dispensing system frame 20 in which the dispenser cartridge 24 is mounted, is guided laterally by cooperating portions of the frame 20 and the actuator 6. In particular, the housing 46 of the first portion 41 of the discharge conduit of the actuator 6 defines a laterally projecting, and vertically extending, guide element 50 (FIG. 4), and the dispensing system frame 20 includes a hollow, laterally projecting guide channel 54 (FIG. 3) for receiving the actuator guide element 50 (FIG. 2) to accommodate relative sliding, vertical movement between the components.

With reference to FIG. 5, the actuator discharge conduit horizontal portion 41 defines an internal horizontal passage 56 which is open at its inlet end to the inside of the inner collar 48 for receiving the discharging flow of the product from the dispenser cartridge stem 36. The passage 56 has an outlet opening into a passage 58 defined in the vertical portion 42 of the discharge conduit of the actuator 6. As can be seen in FIG. 5, the actuator discharge conduit vertical portion passage 58 includes an upper extension portion 59 that extends all the way to the top of the discharge conduit vertical, second portion 42 where it is closed by a distendable, resilient membrane 60 held in place by a retainer 62 mounted to the top of the actuator discharge conduit vertical, second portion 42.

At the bottom of the actuator discharge conduit second portion 42 there is a resilient, pressure-openable valve 140 retained on the actuator 6 by a lower, second retainer 62 (FIGS. 3, 4, and 5) which is identical to the previously described first retainer 62 on the top of the actuator discharge conduit vertical, second portion 42.

As can be seen in FIGS. 4 and 5, the actuator discharge conduit first portion 41 may be characterized as having an inlet opening 70 which is located in fluid communication with the cartridge hollow stem 36 and which defines the inlet end of the passage 56 in the actuator discharge conduit first portion 41.

As can be seen in FIG. 3, the bottom end of the actuator discharge conduit second portion 42 defines an outlet opening 74 which is in communication with the passage 58 defined inside the actuator discharge conduit second portion 42 and through which a fluent substance can pass.

With reference to FIG. 4, the upper end of the actuator discharge conduit second portion 42 defines an intermediate opening 76 that communicates with an extension portion 59 (FIG. 5) of the passage 58 in the actuator discharge conduit second portion 42. The intermediate opening 76 (FIG. 4) may be characterized as being in communication with the entire passageway defined by the connecting discharge conduit passages 56 and 58 (and the extension portion 59 of the passage 58) such that the intermediate opening 76 (FIG. 4) is in communication with the passageway at a location between the inlet opening 70 (FIG. 4) and the outlet opening 74 (FIG. 3). In the illustrated preferred embodiment, the intermediate opening 76 is slightly larger than the outlet opening 74.

The distendable, resilient membrane 60 may be characterized as being located across the intermediate opening 76 (FIG. 4) of the discharge conduit of the actuator 6. With reference to FIGS. 12-15, the membrane 60 has a generally annular peripheral configuration defined by a peripheral, annular wall 80 (FIG. 15) which is closed near its upper end by an upwardly convex (i.e., upwardly projecting), distendable portion 82 (FIG. 15). In the embodiment illustrated in FIG. 15, the annular wall 80 of the membrane 60 has a frustoconical, lower, inner, or inside surface 84 and has a frustoconical, upper, outer or outside surface 86. The lower surface 84 is adapted to be seated in sealing engagement on a mating frustoconical end surface 88 (FIGS. 4 and 5) of the actuator discharge conduit second portion 42.

With reference to FIG. 15, the membrane annular wall upper, outer, surface 86 is adapted to be sealingly engaged with the inside of the retainer 62 described in more detail hereinafter.

With reference to FIG. 15, the distendable portion 82 of the membrane 60 may be regarded as comprising a head 90 having a generally circular configuration, and a generally annular connecting portion 92 for connecting the head 90 to the peripheral, annular wall 80. The head 90 has a generally arcuate, interior surface 94 which, in the embodiment illustrated, defines an arc of a circle as viewed in cross section in FIG. 15, but which may be more particularly described as a partially hemispherical surface.

The exterior side of the head 90 is defined in part by a central, flat, circular portion 96 surrounded by an annular, frustoconical surface 98. As can be seen in FIG. 15, the head 90 is thinner at the central, longitudinal axis, and becomes thicker radially outwardly therefrom.

Further, as can be seen in FIG. 15, the head 90 has a peripheral exterior surface 100 which, as viewed in cross section in FIG. 15, slants or extends radially outwardly with increasing distance from the annular connecting portion 92.

The particular shapes of the portions of the membrane 60, and particular dimensions thereof, may be varied depending on the material, overall internal and external diameters, and other factors. The particular configurations, dimensions, and resilient membrane material form no part of the broadest aspects of the invention.

According to the invention, the membrane 60 is made from a suitable resilient material which can distend when the membrane 60 is engaged with the plunger 4 (FIG. 21) and as described hereinafter and which, upon disengagement of the plunger 4 from the membrane 60, will return to its normal, substantially unstressed, originally installed configuration, as shown in FIG. 5.

The membrane 60 is preferably molded as a unitary structure (i.e., one-piece structure) from material which is flexible, pliable, elastic, and resilient. This can include elastomers, such as a synthetic, thermosetting polymer, including silicone rubber, such as the silicone rubber sold by Dow Corning Corporation in the United States if America under the trade designation D.C. 99-595 and RBL-9595-40. Another suitable silicone rubber material is sold in the United States of America under the designation Wacker 3003-40 by Wacker Silicone Company. The membrane 60 could also be molded from other thermosetting materials or from other elastomeric materials, or from thermoplastic polymers or thermoplastic elastomers, including those based upon materials such as thermoplastic propylene, ethylene, urethane, and styrene, including their halogenated counterparts. For example, a particular non-silicone material that may be employed is ethylene propylene diene monomer rubber ("EPDM"), such as sold in the United States of America under the designation Grade Z1118 by Gold Key Processing, Inc. having an office at 14910 Madison Road, Middlefield, Ohio 44062, United States of America. Another non-silicone material that may be employed is nitrile rubber, such as sold in the United States of America under the designation Grade GK0445081-2 by Graphic Arts Rubber, having an office at 101 Ascot Parkway, Cuyahoga Falls, Ohio 44223, United States of America. It is desirable in many applications that the material be substantially inert so as to avoid reaction with, and/or adulteration of, the fluent substance in contact with the membrane 60.

Figure 11:
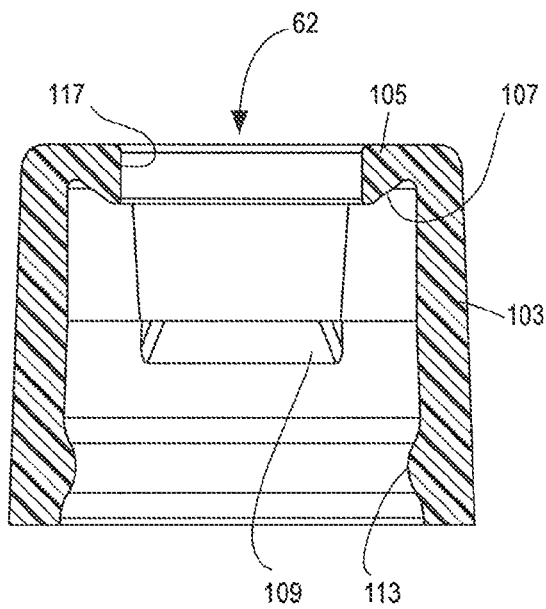
FIG. 11 is a cross-sectional view taken generally along the plane 11-11 in FIG. 9.

The membrane 60 is retained on, and clamped to, the actuator discharge conduit second portion 42 with the retainer 62 illustrated in FIGS. 7-11. As can be seen in FIG. 11, the retainer 62 has a generally annular configuration defined by an annular wall 103. At the top of the annular wall there is an inwardly extending flange 105 defining a downwardly facing, frustoconical surface 107 for clamping the upwardly facing frustoconical surface 86 of the membrane 60 (FIG. 15).

In a preferred embodiment of the retainer 62 as illustrated, internal shoulders or flange segments 109 (FIG. 10) are provided for loosely supporting the membrane 60 during the manufacture of the actuating system when the membrane 60 is initially inserted into the retainer 62 prior to the membrane 60 and retainer 62 being mounted together as an assembly to the upper end of the actuator discharge conduit second portion 42. To accommodate injection molding of the retainer 62 from thermoplastic material (e.g., polypropylene), the upper flange 105 (FIGS. 9 and 10) defines an arcuate slot or aperture 111 (FIGS. 9 and 10) above each shoulder or flange segment 109.

The bottom end of the retainer annular wall 103 includes an internal, annular bead 113 projecting radially inwardly for snap-fit engagement with a mating annular groove 115 (FIG. 5) in the exterior wall of the actuator discharge conduit second portion 42. The retainer 62, when mounted properly on the second portion 42, securely holds the membrane 60 in a leak-tight arrangement on the second portion 42.

As can be seen in FIG. 11, the annular flange 105 defines a central opening 117 for providing access to the membrane 60 so that the membrane 60 may be engaged by the plunger 4 (FIG. 5) when the actuator 6 is moved upwardly to actuate the dispenser cartridge 24 (i.e., when the actuator 6 is moved to the elevated, actuating position illustrated in FIG. 21).

In the embodiment illustrated, the valve 140 is a flexible, resilient, pressure-openable, self-closing, slit-type valve. Forms of such a valve are disclosed in the U.S. Pat. No. 8,678,249 and No. 5,839,614, and in international patent application publication No. WO 2012/150937. The descriptions of those patent documents are incorporated herein by reference thereto to the extent pertinent and to the extent not inconsistent herewith.

The valve 140 is suitable for use with flowable substances, such as liquids, including, inter alia, lotions and creams. The valve 140 is preferably molded as a unitary structure (i.e., one-piece structure) from material which is flexible, pliable, elastic, and resilient. This can include elastomers, such as a synthetic, thermosetting polymer, including silicone rubber, such as the silicone rubber sold by Dow Corning Corporation in the United States if America under the trade designation D.C. 99-595 and RBL-9595-40. Another suitable silicone rubber material is sold in the United States of America under the designation Wacker 3003-40 by Wacker Silicone Company. The valve 140 could also be molded from other thermosetting materials or from other elastomeric materials, or from thermoplastic polymers or thermoplastic elastomers, including those based upon materials such as thermoplastic propylene, ethylene, urethane, and styrene, including their halogenated counterparts. For example, a particular non-silicone material that may be employed is ethylene propylene diene monomer rubber ("EPDM"), such as sold in the United States of America under the designation Grade Z1118 by Gold Key Processing, Inc. having an office at 14910 Madison Road, Middlefield, Ohio 44062, United States of America. Another non-silicone material that may be employed is nitrile rubber, such as sold in the United States of America under the designation Grade GK044508 1-2 by Graphic Arts Rubber, having an office at 101 Ascot Parkway, Cuyahoga Falls, Ohio 44223, United States of America. It is desirable in many applications that the material be substantially inert so as to avoid reaction with, and/or adulteration of, the fluent substance in contact with the valve.

Figure 22:
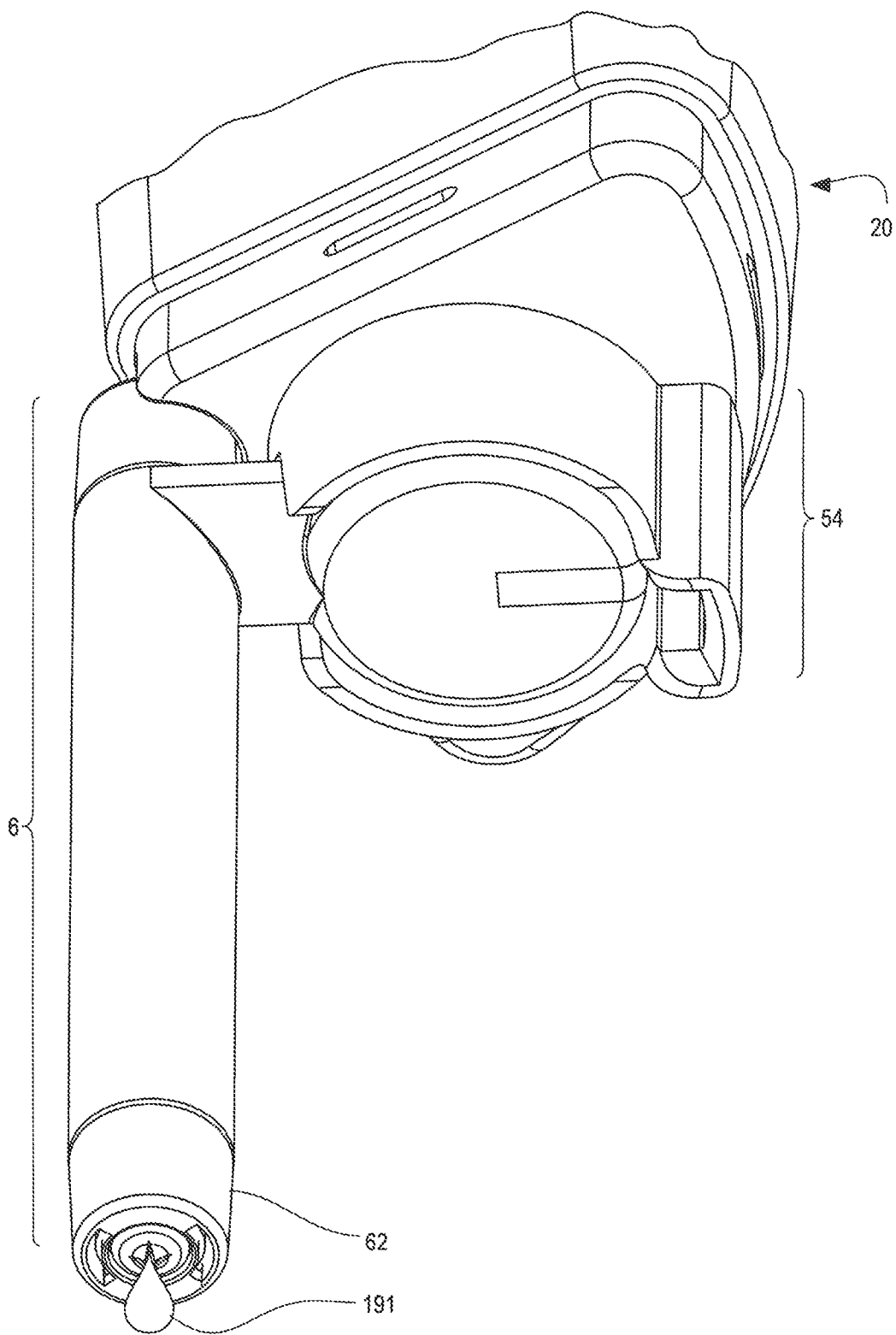
FIG. 22 is a view similar to FIG. 2, but in FIG. 22 the actuator portion of the actuating system has been moved upwardly to a position corresponding to the position shown in FIG. 21 wherein the fluent dispensing system is being actuated.

The valve 140 of the present invention has an initially closed, unactuated, substantially unstressed, rest position or configuration (FIGS. 2-3 and 16-20). The valve 140 can be forced to an "open" position or configuration (FIGS. 21 and 22) when a sufficiently high pressure differential acts across the valve 140 as described hereinafter.

Figure 14:
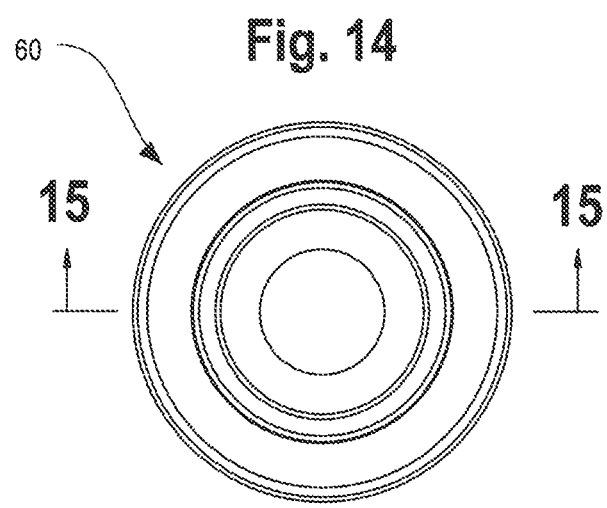
FIG. 14 is a top, plan view of the membrane.
Figure 15:
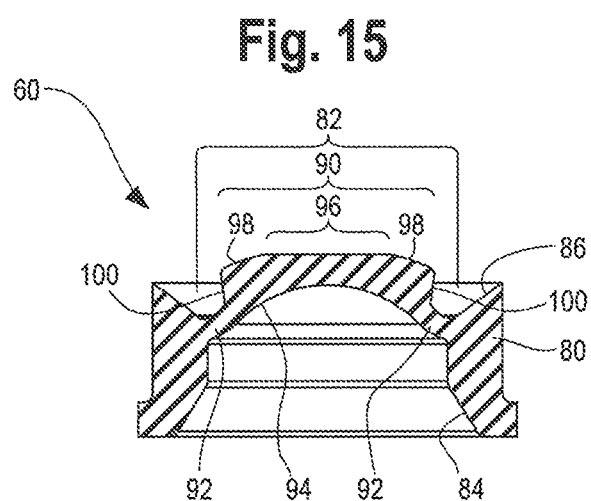
FIG. 15 is a cross-sectional view taken generally along the plane 15-15 in FIG. 14.

With reference to FIGS. 14, 19, and 20, the valve 140 has a peripheral mounting portion or flange 142. The flange 142 may have any suitable configuration for being mounted to, attached to, connected with, or for otherwise accommodating, the actuating system in which the valve 140 is installed. The particular configuration of the flange 142 illustrated in FIGS. 14, 19, and 20 may be characterized as generally a modified dove-tail configuration when viewed in vertical cross section. The flange 142 is adapted to be clamped between the bottom end of the actuator discharge conduit second portion 42 and the lower, second retainer 62 to hold the valve 140 in the system. Preferably, the mounting flange 142 is resiliently compressed so as to accommodate the creation of a secure, leak-resistant seal when the valve flange 142 is compressively engaged between the second retainer 62 and the bottom end of the discharge conduit second portion 42. To that end, the valve flange 142 includes a frustoconical surface 142 (FIG. 20) for engaging a mating frustoconical surface 144 (FIGS. 3 and 5) on the bottom end of the discharge conduit second portion 42. The valve flange 142 also includes a frustoconical surface 145 (FIG. 20) for engaging a mating frustoconical surface 107 (FIGS. 5 and 11) on the second retainer 62.

In a preferred embodiment of the retainer 62 as illustrated (FIGS. 7-12), internal shoulders or flange segments 109 (FIG. 10) are provided for loosely supporting the flange 142 of the valve 140 during the manufacture of the actuating system when the valve 140 is initially inserted into the retainer 62 prior to the retainer 62 being mounted to the lower end of the actuator discharge conduit second portion 42. To accommodate injection molding of the retainer 62 from thermoplastic material (e.g., polypropylene), the retainer upper flange 105 (FIGS. 9 and 10) defines an arcuate slot or aperture 111 (FIGS. 9 and 10) above each shoulder or flange segment 109.

The bottom end of the annular wall 103 of the second retainer 62 includes an internal, annular bead 113 projecting radially inwardly for snap fit engagement with a mating annular groove 147 (FIG. 5) in the exterior wall of the actuator discharge conduit second portion 42 when the retainer 62, with the valve 140 carried therein, is mounted properly on the bottom of the second portion 42 of the discharge conduit.

As can be seen in FIGS. 11 and 21, the annular flange 105 defines a central opening 117 in the lower retainer 62 for providing access to the valve 140 (FIG. 21) so that the valve 140 may open to discharge some fluent product when the actuator 6 is moved upwardly to actuate the dispenser cartridge 24 (i.e., when the actuator 6 is moved to the elevated actuating position illustrated in FIG. 21).

With appropriate modification of the discharge conduit second portion 42, other shapes could be used for the valve flange 142. Some other shapes of flange cross sections which could be employed on the valve 140 are illustrated in the U.S. Pat. No. 5,409,144. In some applications, it may be desirable to configure the flange 142 for attachment to the system by means of adhesive, heat bonding, or other suitable means.

Extending generally radially inwardly from the flange 142 is the generally annular, intermediate portion or sleeve 150 (FIGS. 19 and 20) which connects the flange 142 to a valve head 160 (FIGS. 19 and 20). The valve head 160 is flexible and resilient. The valve head 160 has a generally circular configuration relative to a longitudinal axis 162 (FIG. 20). The fluent substance can be dispensed or discharged through the valve 140 in a discharge flow direction along the longitudinal axis 162 when the valve 140 opens as shown in FIG. 21.

With reference to FIG. 20, the valve head 160 may be characterized as having an interior side 166 facing in the axially inward direction. With reference to FIG. 20, the valve head 160 may be further characterized as having an exterior side 170 facing in the axially outward direction.

With reference to FIG. 20, the outer perimeter of the valve head 160 is preferably defined by a slightly tapered, peripheral, marginal surface 174 which begins at an axially inwardly peripheral corner of the valve head 160 and extends axially outwardly therefrom with a slightly radially inward taper to ultimately terminate at the connector sleeve 150.

The valve head exterior side 170 has an exterior surface 176 (FIG. 20) which interfaces with the environment on the valve exterior side 170 and which has a recessed configuration as viewed looking toward the exterior surface 176 when the valve head 160 is in the fully retracted, closed position.

The valve head interior side 166 has an interior surface defined by an annular portion 180 (FIG. 20) that is partially spherical (and convex as viewed looking toward the valve interior side 166), and that is located radially outwardly from a central portion 181 of the valve head 160 when the valve head 160 is in the fully retracted, closed configuration. That is, with reference to FIG. 20, the annular portion 180 of the valve head interior surface lies on a partially spherical locus that defines a circular arc in longitudinal cross section as viewed along a plane containing the longitudinal axis 162. In the embodiment of the valve 160 illustrated in FIGS. 16 and 20, the boundary between the annular portion 180 and inner central portion 181 is defined by a circular tangent line 182 on the interior surface of the valve head 160. The central portion 181 has a planar, circular configuration when the valve head 160 is in the fully retracted, closed, position.

With reference to FIGS. 20, the valve head exterior surface 176 lies on a partially spherical locus that defines a circular arc in longitudinal cross section as viewed along a plane containing a longitudinal axis 162.

Further, in a preferred form of the embodiment of the valve 140 illustrated in FIG. 20, the radius of the circular arc of the valve head exterior surface 176 is smaller (less) than the radius of the circular arc of the annular portion 180 of the valve head interior side surface.

When the valve head 160 is viewed in cross section as illustrated in FIG. 20, the valve head 160 is somewhat thicker at a radially outside portion of the valve head 160, and is thinner at a radially inside portion of the valve head 160. This configuration assists in providing a desirable opening action and closing action.

With reference to FIGS. 16, 17, and 20, the valve head 140 has a normally closed orifice defined by a plurality of slits 184 radiating laterally or radially from the valve head longitudinal axis 162 (illustrated in FIG. 20). The illustrated embodiment of the valve 140 has four slits 184. A lesser or greater number of slits 184 could be used. The slits 184 extend transversely through the valve head 160 from the interior side 166 to the exterior side 176. Each slit 184 terminates in a radially outer end. In the illustrated embodiment of the valve 140, the slits 184 are of equal length, although the slits could be of unequal lengths.

In the preferred form embodiment of the valve 140, each slit 184 is planar and parallel to the central longitudinal axis 162 of the valve. Each slit 184 preferably defines a linear locus along the head exterior side surface 176 and along the head interior side surface 178. Preferably, the slits 184 diverge from an origin on the longitudinal axis 162 and define equal size angles between each pair of adjacent slits 184. Preferably, four slits 184 diverge at 90 degree angles to define two mutually perpendicular, intersecting, longer slits. In the preferred form of the valve 140, the four slits 184 may be alternatively characterized as being two longer intersecting slits oriented at equal angles of intersection. The length and location of the slits 184 can be adjusted to vary the predetermined opening pressure of the valve 140, as well as other dispensing characteristics.

The slits 184 define four, generally sector-shaped, equally sized flaps or petals 186 (FIG. 21) in the valve head 160. The flaps or petals 186 may be also characterized as "openable regions" or "openable portions" of the valve head 160. Each flap or petal 186 has a pair of diverging transverse faces defined by the slits 184, and each transverse face seals against a confronting transverse face of an adjacent petal 186 when the valve 140 is closed.

The valve 140 can be molded with the slits 184. Alternatively, the valve slits 184 can be subsequently cut into the central head 160 of the valve 140 by suitable conventional techniques. In operation, the petals 186 can be forced open outwardly (downwardly in FIG. 21) from the intersection point of the slits 184 when a sufficient force is applied to the interior surface 178 of the valve head 160 (as by subjecting the valve head 160 to a pressure differential across the valve head 160).

When the valve 140 is in the fully retracted, closed position (FIG. 20), the connector sleeve 150 has a tubular configuration in the form of a tubular membrane 150, and the membrane 150 defines an interior surface 188 and an exterior surface 190. When viewed in longitudinal cross section (as seen in FIG. 20), the connector sleeve 150 has a straight, first leg portion 192 that is connected with the valve flange 142, and has a second leg portion 194 that extends arcuately from the first leg portion 192 to connect with the valve head 160. The thickness of each leg portion 192 and 194 may vary.

In the illustrated embodiment of the valve 140, the connector sleeve 150 locates the valve head 160 so that a portion of the valve head 160 projects axially outwardly beyond the marginal flange 142.

The sleeve 150 of the valve 140 is preferably configured for use in conjunction with a particular system, and a specific type of fluent substance, so as to achieve the flow characteristics desired. For example, the viscosity and density of the fluent substance are factors to be considered. The rigidity and durometer of the valve material, and size and thickness of portions of both the valve head 160 and the connector sleeve 150, are additional factors to be considered.

The valve 140 opens outwardly when the valve 140 is subjected to a sufficient pressure differential (i.e., a lower pressure on the exterior side of the valve head 160 than on the interior side of the valve head 160). The valve 140 also accommodates in-venting by opening inwardly (when the lower pressure is on the interior).

The valve 140 could be opened outwardly by sucking on the exterior side of the valve or otherwise subjecting the valve exterior side to a reduced pressure. However, in many typical dispensing applications, the valve 140 is opened by subjecting the interior side of the valve head 160 to an increased pressure. In the following discussion, the operation of the valve 140 will be described with reference to such an increased interior pressure which is sufficient to open the valve 140 outwardly into a lower ambient pressure environment.

The opening of the valve 140 may be characterized as occurring in response to a predetermined minimum opening pressure. The valve 140 is typically designed to have a predetermined minimum opening pressure which causes the valve petals 186 to fully open, and the selection of a desired predetermined minimum opening pressure is determined in accordance with, inter alia, (1) the flow criteria desired for a particular fluent substance, and (2) the maximum static head that is exerted on the interior side of the valve 140 by the fluent substance and that must not cause the valve 140 to open.

In operation, the valve 140 functions in the following manner. The valve 140 normally assumes an initial, normally closed configuration illustrated in FIGS. 5, 6, and 16-20, wherein the valve 140 remains substantially in its original, molded shape without deformation (except perhaps at the flange 142 if the flange 142 is sufficiently compressively engaged by the mounting components). When the valve 140 is in the normally closed configuration, the connector sleeve 150 is substantially unstressed, the valve discharge orifice slits 184 are fully closed, and the valve head 160 is in a retracted position that is somewhat axially inwardly relative to the position that the valve head 160 will have when it is opened.

Figure 6:
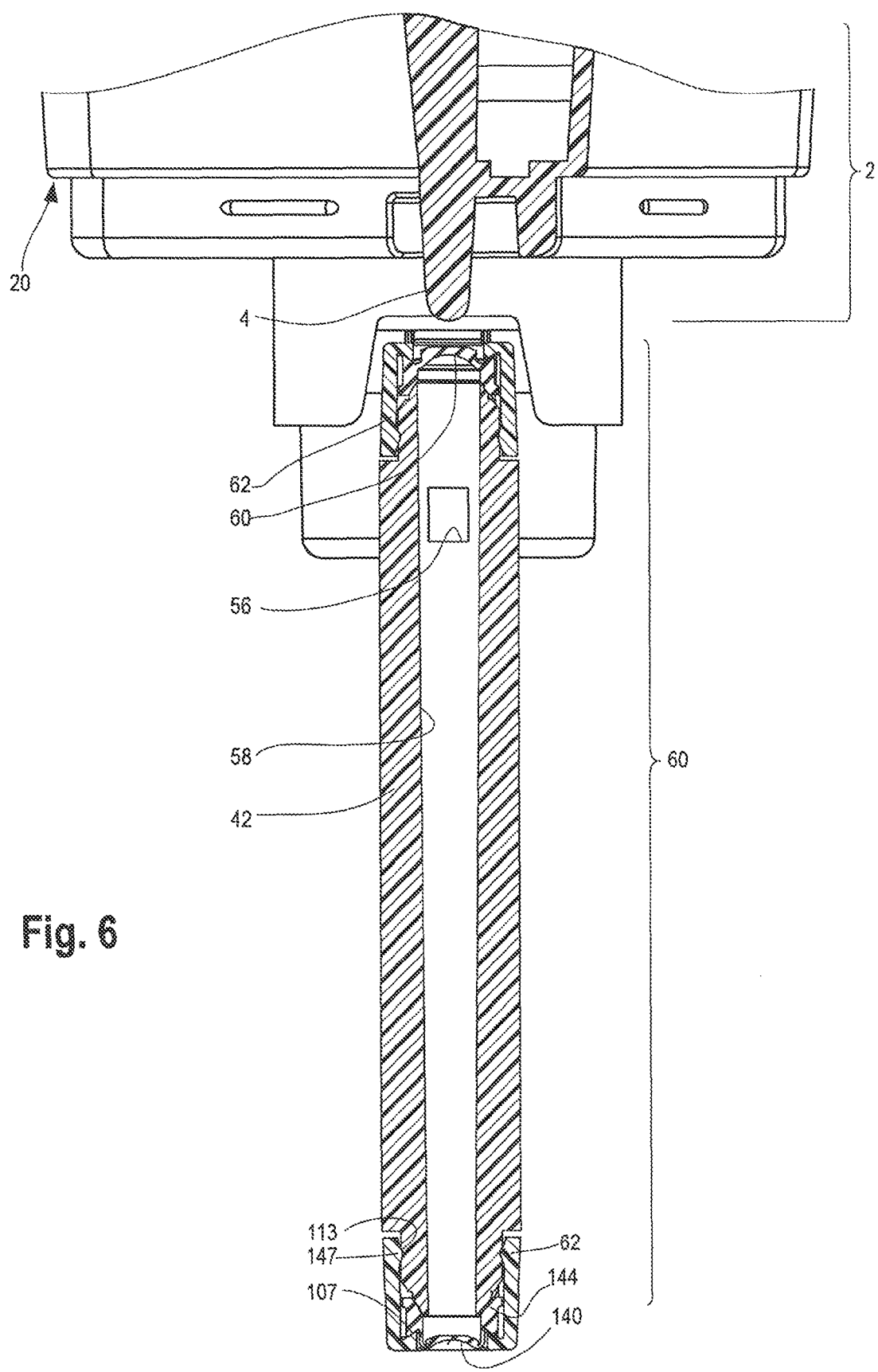
FIG. 6 is a fragmentary, cross-sectional view taken generally along the plane 6-6 in FIG. 1.
Figure 9:
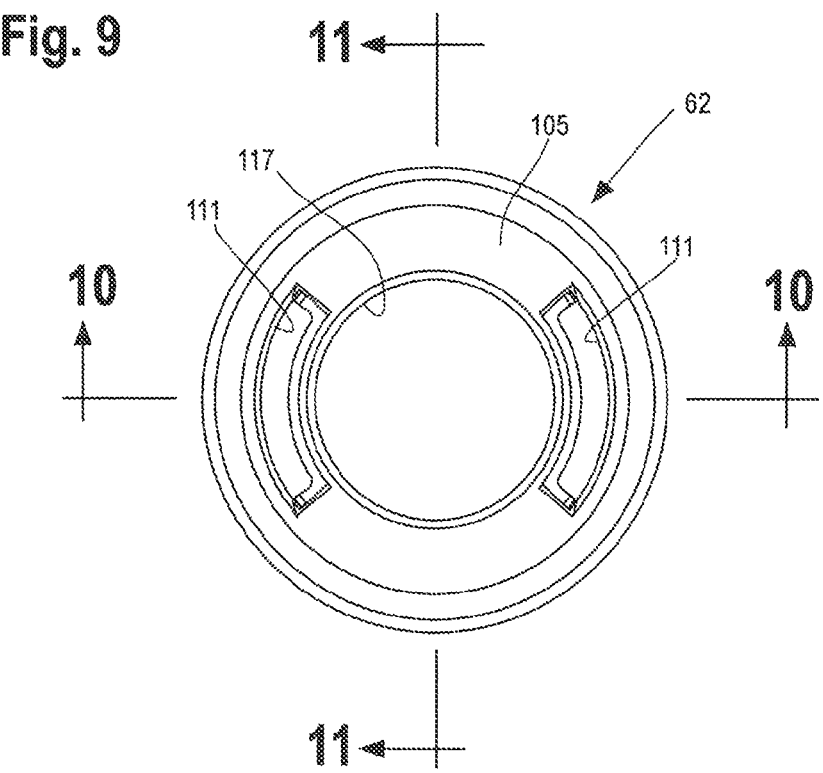
FIG. 9 is a top, plan view of the retainer shown in FIG. 7.
Figure 10:
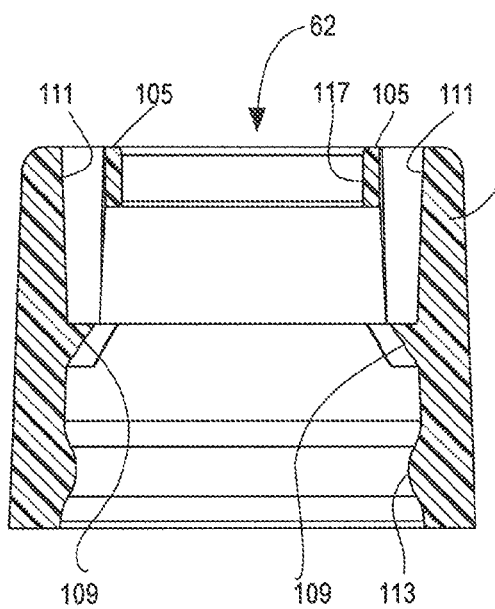
FIG. 10 is a cross-sectional view taken generally along the plane 10-10 in FIG. 9.

When a sufficient pressure differential is established across the valve head 160—such as when increased pressure is established on the valve interior side 166, the curved leg portion 194 of the connector sleeve 150 begins to distort (i.e., become straight or less curved), and the valve head 160 begins to shift somewhat axially outwardly (downwardly in FIGS. 5 and 6).

As the interior 166 side of the valve head 160 is subjected to additional pressure, the valve head 160 continues to move slightly outwardly as the curved second leg portion 194 of the connector sleeve 150 tends to straighten and extend.

When the interior side of the valve head 160 is subjected to further increased pressure, the valve head 160, per se, continues to shift slightly outwardly. However, because connector sleeve second leg portion 194 is already somewhat straightened and extended, further outward shifting of the valve head 160 longitudinally slightly stretches and tensions the connector sleeve 150, thereby increasing the outwardly directed torque applied to the valve head 160. Also, the further outward movement of the valve head 160 tends to flatten or straighten the valve head 160, particularly along the exterior surface 176 thereof. This flattening motion tends to slightly enlarge or dilate the circular plan configuration of the valve head 160, which enlargement is in turn resisted by radially inwardly directed forces applied to the marginal surface 174 of the valve head 160 by the connector sleeve 150, thereby generating another complex pattern of stresses within the valve 140, and these include stresses which tend to compress the valve head 160 in a radially inward direction.

When additional pressure is applied to the interior side of the valve head 160, the valve head 160 continues to shift outwardly by further longitudinal stretching of the connector sleeve 150, and further enlargement of the plan shape of the valve head 160. The marginal portion 174 of the valve head 160 is elastically deformed further inwardly, as a consequence of the increased torque forces applied thereto by the connector sleeve 150. These combined forces and motions also serve to further compress the valve head 160, which occurs just prior to the valve petals 186 starting to open, wherein the valve head 160 is in a temporary, relatively unstable condition of equilibrium that can be characterized as a "bifurcation state". The combined forces acting on the valve head 160 in the bifurcation state will, upon application of any additional outward force on the surface of the valve head interior side 166, cause the valve 140 to quickly open outwardly by separating the valve petals 186 to create an open orifice in the manner illustrated in FIG. 21, and thereby dispense the fluent substance through valve head open petals 186. FIG. 21 shows part of a discharge or drop 191 of the fluent substance flowing through the valve 140.

It will be appreciated that while various theories and explanations have been set forth herein with respect to how forces and stresses may affect the operation of the valve 140, there is no intention to be bound by such theories and explanations. Further it is intended that all structures falling within the scope of the appended claims are not to be otherwise excluded from the scope of the claims merely because the operation of such valve structures may not be accounted for by the explanations and theories presented herein.

The petals 186 of the valve 140 can also open inwardly when subjected to a sufficient differential pressure wherein the interior pressure is less than the exterior pressure by a predetermined amount. This permits (1) a residue or residual tail of the substance hanging on the petals 186 on the exterior side of the valve 140 to be sucked back through the valve to the interior side of the valve, and (2) in-venting of ambient exterior atmosphere through the valve to equalize the pressure—at which point the inwardly opened petals 186 of the valve 140 would close.

When the actuator 6 is moved upwardly by suitable means (e.g., a person's finger or electromechanical operator (not illustrated)) as indicated schematically by the arrow 8 in FIG. 21, the dispenser cartridge 24 is actuated to dispense the fluent substance product into the actuator discharge conduit passages 56 and 58 as previously explained in detail. At the same time, the upper end of the second portion 42 of the discharge conduit of the actuator 6 moves against the plunger 4 (which is part of the actuator system, but which, in the illustrated embodiment, projects downwardly from the frame 20 of the dispensing system 2 as shown in FIG. 21). The membrane 60 engages the end of the stationary plunger 4 as the actuator 6 moves upwardly as shown in FIG. 21. The membrane 60 thus becomes distended inside the extension portion 59 of the passage 58 of the second portion 42 of the actuator 6, as shown in FIG. 21. In a system that had not been previously operated to fill the volume defined by the passages 56 and 58 (and the extension 59), a number of actuations might be required to initially fill the passages. Once the passages have filled, then further actuation causes the pressure of the product within the discharge conduit of the actuator 6 to increase, and sufficient increased pressure causes the valve 140 at the bottom of the discharge conduit to open as shown in FIG. 21.

After the actuator passages have been filled, a further single upward stroke of the actuator 6 to the limit of the stroke length causes a predetermined amount of product to be discharged from the dispenser cartridge into the actuator 6 to pressurize the system sufficiently to open the petals 186 of the valve 140 so that a generally corresponding amount of product is discharged or dispensed from the bottom of the discharge conduit of the actuator 6 through the open valve 140.

Figure 23:
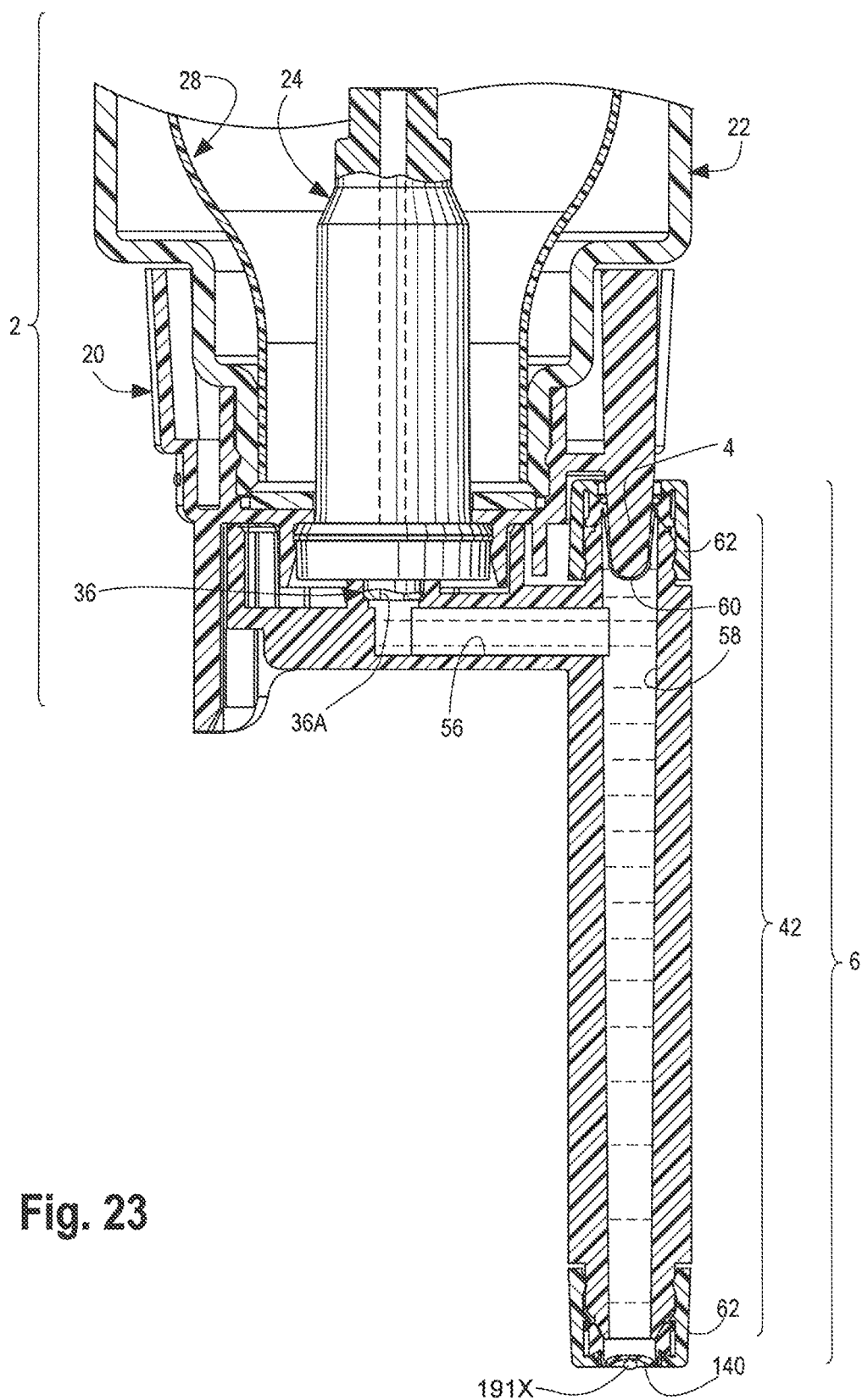
FIG. 23 is a cross-sectional view similar to FIG. 21, but in FIG. 23 the actuation of the fluent substance dispensing system has been completed, and the valve at the end of the actuating system discharge conduit is closed, and a residue drop of the fluent substance hangs from the exterior of the closed valve.

At the end of the upward travel of the actuator 6, the dispenser cartridge 24 has been fully actuated. At that point, if the dispenser cartridge 24, is a pump type dispenser cartridge, then the pump internal piston has reached the limit of its pressurizing travel so that it no longer discharges and no longer pressurizes the fluent product. Thus, the pressure in the actuator discharge conduit passages 56, 58, and 59 decrease as the product is discharging through the open valve 140. When the pressure drops sufficiently, the valve 140 closes owing to its inherent resiliency. However, a quantity of the product may remain hanging from the closed valve 140 as illustrated in FIG. 23 wherein the quantity of hanging product is designated by the number 191X. Such a hanging quantity of product may be characterized as a residual drop, residue, or hanging tail 191X. This may be somewhat undesirable and/or may result in an unwanted deposit of the substance if the tail 191X later drops or falls away. However, the hanging tail 191X can be drawn back inside the actuator 6 as will next be explained.

At the end of the upward stroke of the actuator 6, and subsequent release of the upward force (represented by the arrow 8 in FIG. 21) on the actuator 6, the actuator 6 can return to the lower, rest position under the influence of gravity and/or the springs (not illustrated) inside the dispenser cartridge 24. As previously explained, the lowered, rest position of the actuator 6 can be defined by suitable means (e.g., the rest position of an underlying electromechanical operator (not illustrated) or other operator (not illustrated) or by a suitable travel stop (not shown) that would extend downwardly from the dispensing system frame 20 to engage the underside of the actuator 6 at the lowered, rest position).

Figure 24:
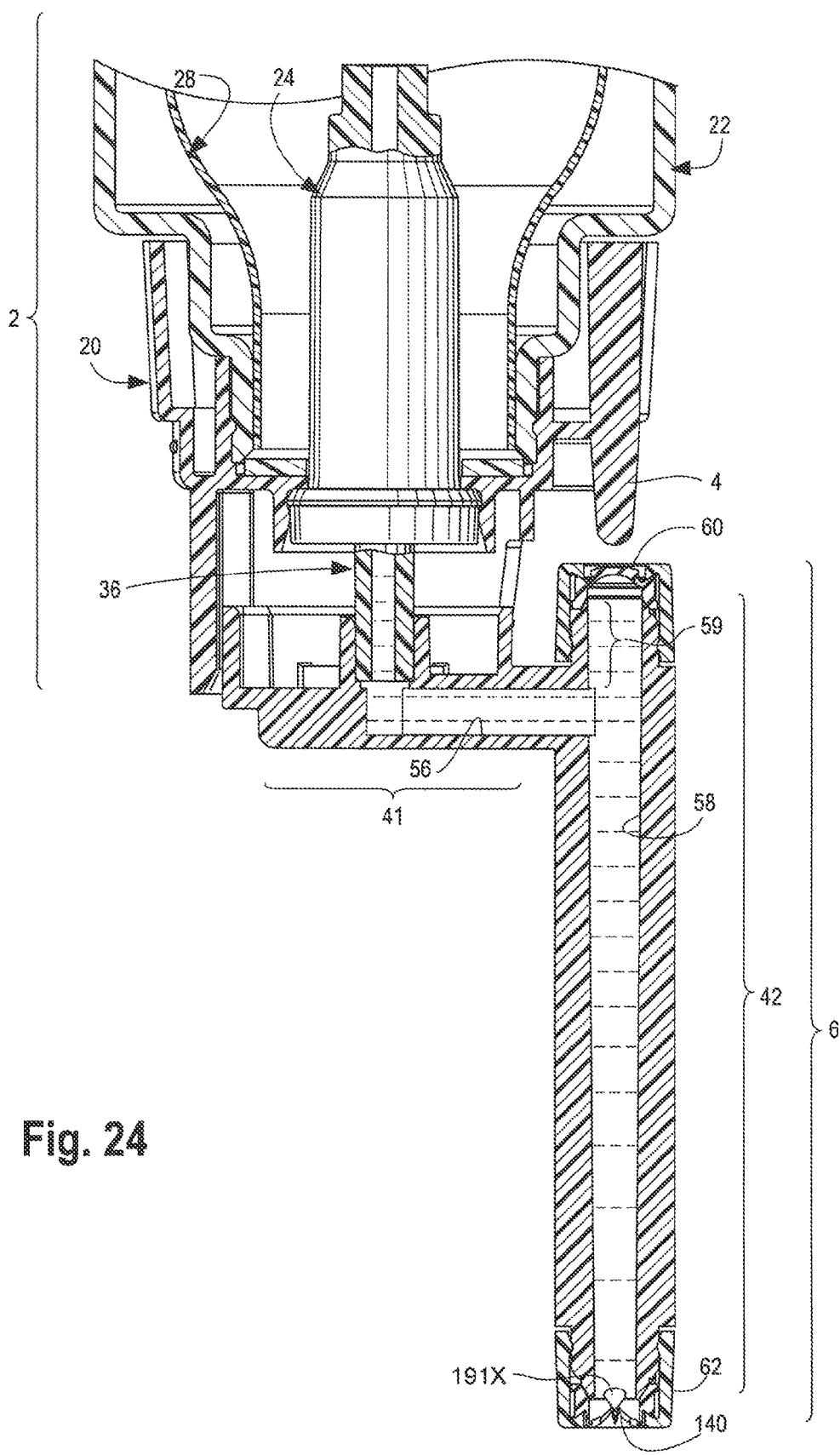
FIG. 24 is a cross-sectional view showing the actuator of the actuating system returned to the lower, unactuated position (as in FIG. 5), but wherein the actuating system actuator discharge conduit valve has opened inwardly so as to accommodate the drawing in of the fluent substance residue and so as to accommodate in-venting of ambient atmosphere.

In accordance with the present invention, the tail 191X can be sucked back into the actuator 6 as shown in FIG. 24 as the actuator 6 returns to the lowered, rest position. The return of the actuator 6 to the lowered, rest position carries the distended membrane 60 away from the plunger 4 so that the resilient membrane 60 returns to its original, unstressed condition (compare FIG. 23 with FIG. 24), and this process effects a reduction of pressure within the internal passages of the actuator 6, especially in the internal passage 58 and its extension 59. This reduction in pressure causes the internal pressure within the passage 58 and extension 59 to drop below the ambient atmospheric pressure by an amount sufficient to cause the closed valve 140 to be open inwardly as shown in FIG. 24 as the tail 191X is sucked inwardly into the passage 58, followed by the in-venting of a small amount of ambient atmospheric air to substantially equalize the pressure in the passage 58 with the ambient atmospheric pressure so that the valve petals 186, owing to their inherent resiliency, move back to the fully closed position (such as shown in FIGS. 5 and 6). As a result of the interaction between plunger 4, membrane 60, and the internal passages within the actuator 6, the undesirable hanging tail 191X of residual material is moved from the exterior of the actuator 6 to the interior of the actuator 6 for reuse. This also results in the exterior bottom end of the actuator 6 having a more presentable appearance.

Figure 25:
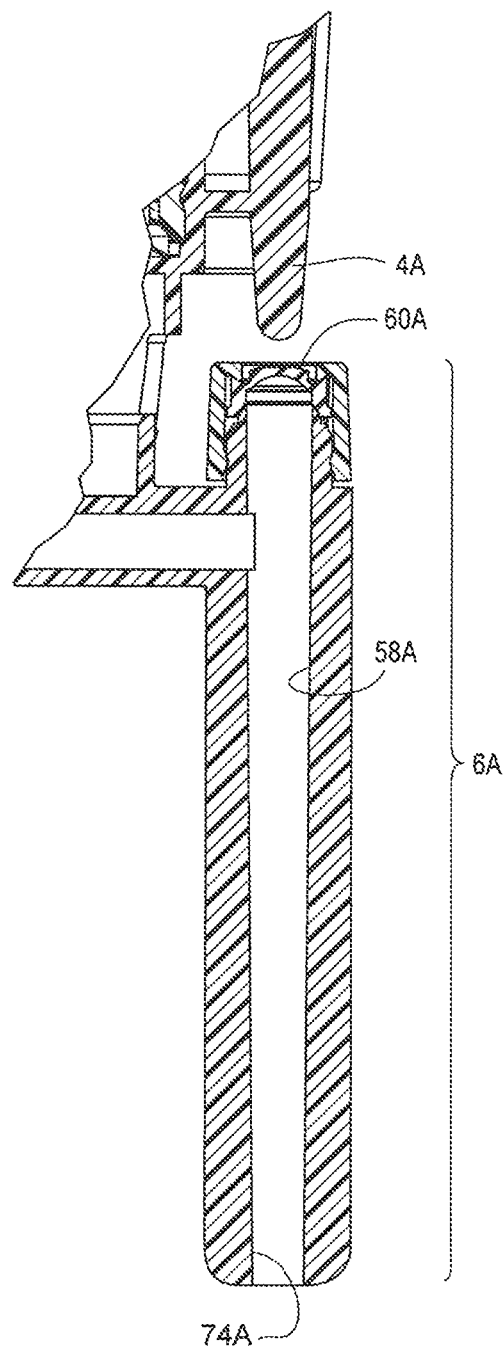
FIG. 25 is a fragmentary, cross-sectional view similar to FIG. 5, but FIG. 25 shows an alternate embodiment of the actuating system actuator discharge conduit.

FIG. 25 illustrates an alternate embodiment of the actuator system wherein the actuator system of the alternate embodiment is shown as including an actuator 6A and a cooperating plunger 4A which are functionally analogous to the actuator 6 and plunger 4, respectively, of the first embodiment previously described with reference to FIGS. 1-24.

The alternate embodiment of the actuator 6A does not include a valve (such as the valve 140 of the first embodiment), and does not include a valve retainer (such as the valve retainer 62 of the first embodiment). Without a valve, the alternate embodiment actuator 6A has a permanently open bottom end defining an outlet opening 74A. Depending upon, inter alia, (1) the viscosity of the fluent product to be dispensed, (2) the cross-sectional area of the passage 58A of the actuator 6A, and (3) the material from which the conduit of the actuator 6A is made, a normally closed outlet valve is not required. Such an alternate embodiment of the system operates in substantially the same manner as the first embodiment described above with reference to FIGS. 1-24 except for the action of the first embodiment system valve 140 which is not incorporated in the alternate embodiment illustrated in FIG. 25.

The dispensing system and remaining components of the alternate embodiment actuator 6A, and the plunger 4A are identical with the dispensing system and analogous components of the first embodiment described above with reference to FIGS. 1-24.

The alternate embodiment actuator 6A, when it is filled with product, retains the product in the passage 58A of the actuator 6A because, owing to the appropriately sized small diameter of the discharge passage and viscosity of the product, the product does not drip out of the open bottom end of the actuator 6A. But, during actuation of the actuator 6A, the fluent product can be discharged through the open bottom end of the actuator 6A. After such a discharge, a small residue or hanging tail of the discharging substance (i.e., product) may remain hanging from the substance inside the open, bottom end of the actuator 6A (similar to the tail 191X illustrated in FIG. 23 with respect to the first embodiment of the actuator 6). The return of the actuator 6A downwardly away from the engaged plunger 4A to the unactuated, rest position will result in a reduction in the pressure within the passage 58A of the actuator to as the membrane 60A returns to its undeformed configuration, and that will cause the hanging tail or residue of the product to be sucked inwardly into the interior passage 58A at the bottom end of the actuator 6A in a manner analogous to that of the first embodiment explained above with reference to FIGS. 1-24.

The present invention can be summarized in the following statements or aspects numbered 1-13.

1. An actuating system for a fluent substance dispensing system wherein the dispensing system includes (I) a frame, and (II) a dispenser cartridge that (A) can be mounted on the frame in communication with a fluent substance; and (B) has a reciprocatable, product-dispensing hollow stem that is (i) biased to an extended position in which the cartridge is unactuated, and (ii) movable horn the extended position to a depressed position in which the cartridge is actuated for discharging the fluent substance through the stem;

said actuating system comprising:
(A) a plunger on the frame; and
(B) an actuator (6, 6A) that includes (1) a discharge conduit that is located adjacent the frame to accommodate relative movement between said discharge conduit and the frame toward and away from each other, and that defines
(a) an inlet opening that can be located in fluid communication with the cartridge hollow stem for receiving a fluent substance discharged from the cartridge hollow stem when the cartridge is actuated;
(b) an outlet opening from which a fluent substance can be discharged;
(c) a passageway between said inlet opening and said outlet opening; and
(d) an intermediate opening that (i) is in communication with said passageway between said inlet opening and said outlet opening, and (ii) can receive said plunger, and
(2) a distendable, resilient membrane that
(a) is located across said intermediate opening;
(b) is distended by said plunger during relative movement between the frame and said discharge conduit toward each other to depress the cartridge hollow stem for discharging the fluent substance from the cartridge into said discharge conduit passageway; and
(c) is less distended by said plunger during relative movement between the frame and said discharge conduit away from each other permitting the cartridge hollow stem to be biased toward the extended position in which the cartridge is unactuated and whereby ambient atmospheric pressure can force at least some of the fluent substance inwardly from said discharge conduit outlet as the volume in said passageway increases owing to the decreased distention of said membrane.

2. The actuating system in accordance with aspect 1 in which said discharge conduit is guided by the frame for vertical reciprocating movement between a first position corresponding to the extended position of the dispenser cartridge hollow stein and a second position corresponding to the depressed position of the dispenser cartridge hollow stem.

3. The actuating system (4, 4A; 6, 6A) in accordance with any of the preceding aspects 1-2 further including a first retainer (62) mounted on said discharge conduit (41, 42) for retaining said membrane (60, 60A).

4. The actuating system in accordance with any of the preceding aspects 1-3 further including a pressure-openable, flexible, resilient, self-sealing slit valve that (1) has a normally closed configuration, and (2) is located at said outlet opening.

5. The actuating system in accordance with any of the preceding aspects 1-4 further including a second retainer mounted on said discharge conduit for retaining said valve.

6. The actuating system in accordance with any of the preceding aspects 1-5 in which said membrane is separately molded from a resiliently deformable material.

7. The actuating system in accordance with any of the preceding aspects 1-6 in which said membrane farther comprises: (A) a distendable portion for receiving said plunger; and (B) an annular wall for being retained on said discharge conduit.

8. The actuating system in accordance with any of the preceding aspects 1-7 in which said membrane further comprises a generally arcuate, interior surface in communication with said passageway.

9. The actuating system in accordance with any of the preceding aspects 1-8 in which said membrane further comprises: (A) a head portion; and (B) an annular connecting portion, wherein said head portion is thicker than said annular connecting portion.

10. The actuating system in accordance with any of the preceding aspects 1-9 in which said passageway further comprises an upper extension portion, and said intermediate opening extends across said upper extension portion.

11. The actuating system in accordance with any of the preceding aspects 1-10 in which said intermediate opening is axially aligned with said outlet opening.

12. The actuating system in accordance with any of the preceding aspects 1-11 in which said plunger terminates in the form of a partially hemispherical surface.

13. The actuating system in accordance with any of the preceding aspects 1-12 in which said discharge conduit intermediate opening is larger than said outlet opening.

Various modifications and alterations to this invention will become apparent to those skilled in the art without departing from the scope and spirit of this invention. Illustrative embodiments and examples are provided as examples only and are not intended to limit the scope of the present invention.

What is claimed is:

1. An actuating system (4, 4A; 6, 6A) for a fluent substance dispensing system (2) wherein the dispensing system (2) includes (I) a frame (20), and (II) a dispenser cartridge (24) that (A) can be mounted on the frame (2) in communication with a fluent substance; and (B) has a reciprocatable, product-dispensing hollow stem (36) that is (i) biased to an extended position in which the cartridge (24) is unactuated, and (ii) movable from the extended position to a depressed position in which the cartridge (24) is actuated for discharging the fluent substance through the stem (36);

said actuating system (4, 4A; 6, 6A) comprising:
(A) a plunger (4, 4A) on the frame (20); and
(B) an actuator (6, 6A) that includes
  (1) a discharge conduit (41, 42) that is located adjacent the frame (20) to accommodate relative movement between said discharge conduit (41, 42) and the frame (20) toward and away from each other, and that defines
    (a) an inlet opening (70) that can be located in fluid communication with the cartridge hollow stem (36) for receiving a fluent substance discharged from the cartridge hollow stem (36) when the cartridge (24) is actuated;
    (b) an outlet opening (74, 74A) from which a fluent substance can be discharged;
    (c) a passageway (56, 58, 59) between said inlet opening and said outlet opening (74, 74A); and
    (d) an intermediate opening (76) that (i) is in communication with said passageway (56, 58, 59) between said inlet opening (70) and said outlet opening (74, 74A), and (ii) can receive said plunger (4, 4A), and
  (2) a distendable, resilient membrane (60, 60A) that
    (a) is located across said intermediate opening (76);
    (b) is distended by said plunger (4, 4A) during relative movement between the frame (20) and said discharge conduit (41, 42) toward each other to depress the cartridge hollow stem (36) for discharging the fluent substance from the cartridge (24) into said discharge conduit passageway (56, 58, 59); and
    (c) is less distended by said plunger (4, 4A) during relative movement between the frame (20) and said discharge conduit (41, 42) away from each other permitting the cartridge hollow stem (36) to be biased toward the extended position in which the cartridge (24) is unactuated and whereby ambient atmospheric pressure can force at least some of the fluent substance inwardly from said discharge conduit outlet opening (74, 74A) as the volume in said passageway (56, 58, 59) increases owing to the decreased distention of said membrane (60, 60A).

2. The actuating system (4, 4A; 6, 6A) in accordance with claim 1 in which said discharge conduit (41, 42) is guided by the frame (20) for vertical reciprocating movement between a first position corresponding to the extended position of the dispenser cartridge hollow stem (36) and a second position corresponding to the depressed position of the dispenser cartridge hollow stem (36).

3. The actuating system (4, 4A; 6, 6A) in accordance with claim 1 further including a first retainer (62) mounted on said discharge conduit (41, 42) for retaining said membrane (60, 60A).

4. The actuating system (4, 4A; 6, 6A) in accordance with claim 1 further including a pressure-openable, flexible, resilient, self-sealing slit valve (140) that (1) has a normally closed configuration, and (2) is located at said outlet opening (74).

5. The actuating system (4, 4A; 6, 6A) in accordance with claim 4 further including a second retainer (62) mounted on said discharge conduit (41, 42) for retaining said valve (140).

6. The actuating system (4, 4A; 6, 6A) in accordance with claim 1 in which said membrane (60, 60A) is separately molded from a resiliently deformable material.

7. The actuating system (4, 4A; 6, 6A) in accordance with claim 1 in which said membrane (60, 60A) further comprises: (A) a distendable portion (82) for receiving said plunger (4, 4A); and (B) an annular wall (80) for being retained on said discharge conduit (41, 42).

8. The actuating system (4, 4A; 6, 6A) in accordance with claim 1 in which said membrane (60, 60A) further comprises a generally arcuate, interior surface (94) in communication with said passageway (56, 58, 59).

9. The actuating system (4, 4A; 6, 6A) in accordance with claim 1 in which said membrane (60, 60A) further comprises: (A) a head portion (90); and (B) an annular connecting portion (92), wherein said head portion (90) is thicker than said annular connecting portion (92).

10. The actuating system (4, 4A; 6, 6A) in accordance with claim 1 in which said passageway (56, 58, 59) further comprises an upper extension portion (59), and said intermediate opening (76) extends across said upper extension portion (59).

11. The actuating system (4, 4A; 6, 6A) in accordance with claim 1 in which said intermediate opening (76) is axially aligned with said outlet opening (74, 74A).

12. The actuating system (4, 4A; 6, 6A) in accordance with claim 1 in which said plunger (4, 4A) terminates in the form of a partially hemispherical surface.

13. The actuating system (4, 4A; 6, 6A) in accordance with claim 1 in which said discharge conduit intermediate opening (76) is larger than said outlet opening (74, 74A).

* * * * *